(12) United States Patent
Tsukada et al.

(10) Patent No.: US 7,905,597 B2
(45) Date of Patent: Mar. 15, 2011

(54) FUNDUS OBSERVATION DEVICE AND A PROGRAM CONTROLLING THE SAME

(75) Inventors: Hisashi Tsukada, Tokyo (JP); Tsutomu Kikawa, Tokyo (JP); Yasufumi Fukuma, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 11/770,124

(22) Filed: Jun. 28, 2007

(65) Prior Publication Data

US 2008/0030680 A1  Feb. 7, 2008

(30) Foreign Application Priority Data

Aug. 2, 2006  (JP) ................................. 2006-210877

(51) Int. Cl.
*A61B 3/14* (2006.01)
*A61B 3/10* (2006.01)

(52) U.S. Cl. ........................................ 351/206; 351/221
(58) Field of Classification Search .......... 351/205–206, 351/221; 354/62
See application file for complete search history.

(56) References Cited

U.S. PATENT DOCUMENTS

| | | | |
|---|---|---|---|
| 6,198,540 B1 | 3/2001 | Ueda | |
| 6,755,526 B2 | 6/2004 | Shibata | |
| 2004/0239876 A1* | 12/2004 | Levine | 351/206 |
| 2006/0066869 A1 | 3/2006 | Ueno | |

FOREIGN PATENT DOCUMENTS

| | | |
|---|---|---|
| EP | 1650528 | 4/2006 |
| EP | 1650528 A2 | 4/2006 |
| JP | 2003-000543 | 1/2003 |
| JP | 2004-350849 | 12/2004 |
| JP | 2005-241464 | 9/2005 |
| WO | WO-2005/117534 A2 | 12/2005 |
| WO | 2005117534 | 12/2006 |

OTHER PUBLICATIONS

Extended European Search Report—Application No. EP 07 01 2042.

* cited by examiner

*Primary Examiner* — Scott J Sugarman
*Assistant Examiner* — Dawayne A Pinkney
(74) *Attorney, Agent, or Firm* — Edwards Angell Palmer & Dodge LLP

(57) ABSTRACT

A fundus observation device comprises: an image forming part comprising a first image forming part and a second image forming part, the first image forming part forming a 2-dimensional surface image of fundus oculi of an eye through optical processing, the second image forming part optically scanning a surface region of the fundus oculi corresponding to at least a part of the 2-dimensional surface image to form a tomographic image of the fundus oculi; a controller configured to control the image forming part; and a storage configured to store control information including control instructions to be sent from the controller to the image forming part, when one of the 2-dimensional surface image and the tomographic image is formed. The controller, at the time of formation of new one of the 2-dimensional surface image and the tomographic image of the fundus oculi, instructs the image forming part to form the new one of the 2-dimensional surface image and the tomographic image based on the control information stored in the storage.

20 Claims, 12 Drawing Sheets

FUNDUS OBSERVATION DEVICE AND A PROGRAM CONTROLLING THE SAME

BACKGROUND OF THE INVENTION

1. Field of the Invention

The present invention relates to a fundus observation device for observing the state of the fundus oculi of an eye, and a program controlling the same.

2. Description of the Related Art

As a fundus observation device, conventionally, a fundus camera has been widely used. FIG. 11 shows one example of the appearance of a conventional generally-used fundus camera, and FIG. 12 shows one example of an optical system composition to be internally accommodated in the fundus camera (e.g. JP Patent laid-open No. 2004-350849). Herein, "observation" includes at least a case in which produced fundus images are observed (fundus observations with the naked eye may be included).

First, referring to FIG. 11, an explanation will be made regarding the appearance of a conventional fundus camera 1000. This fundus camera 1000 is provided with a platform 3 mounted on a base 2 so as to be slidable in the front and rear, right and left directions (horizontal direction). On this platform 3, an operation panel 3a and a control lever 4 are installed for an examiner to conduct various operations.

The examiner can 3-dimensionally move the platform 3 on the base 2 by operating the control lever 4. On the top of the control lever 4, an operation button 4a is installed to be pressed down to obtain fundus oculi images.

On the base 2, a post 5 is installed standing upwards. On the post 5, a jaw rest 6 where the jaw of a patient is to be rested and an external fixation lamp 7 emitting light for fixing an eye E are provided.

On the platform 3, a main body part 8 is installed to accommodate various optical systems and control systems of the fundus camera 1000. The control system may be installed inside the base 2 or the platform 3, etc., or in an external device such as a computer connected to the fundus camera 1000.

On the side of the eye E of the main body part 8 (the left side of the page in FIG. 11), an objective lens part 8a disposed opposite to the eye E is installed. Also, on the examiner's side of the main body part 8 (the right side of the page in FIG. 11), an eyepiece part 8b for observing the fundus oculi of the eye E with the naked is installed.

Furthermore, the main body part 8 is provided with a still camera 9 for producing a still image of a fundus oculi of the eye E and an imaging device 10 such as a TV camera for producing still images or moving images of a fundus oculi. The still camera 9 and the imaging device 10 are formed so as to be removable from the main body part 8.

As the still camera 9, in accordance with various conditions such as the purpose of an examination or the saving method of produced images, a digital camera equipped with imaging elements such as CCD (Charge Coupled Device) or CMOS (Complementary Metal Oxide Semiconductor), a film camera, and an instant camera, etc. may interchangeably be used when it is appropriate. The main body part 8 is equipped with a mounting part 8c for interchangeably mounting various kinds of still camera 9.

If the still camera 9 or the imaging device 10 is for taking digital images, the image data of the produced fundus image can be sent to a device such as a computer connected to the fundus camera 1000 and be observed as a fundus image displayed on the display. Also, the image data can be sent to an image storing device connected to the fundus camera 1000 to compile a database and be used as electronic data for creating medical charts, etc.

Furthermore, on the examiner's side of the main body part 8, a touch panel monitor 11 is installed. On this touch panel monitor 11, fundus images of the eye E created based on the video signals output from the (digital-type) still camera 9 or imaging device 10 are displayed. Moreover, on the touch panel monitor 11, a 2-dimensional coordinate system with the center of the screen as the origin is displayed overlapped with a fundus image. When the examiner touches a desired position on the screen, the coordinate value corresponding to the touched position is displayed.

Next, referring to FIG. 12, a composition of an optical system of the fundus camera 1000 will be described. The optical system of the fundus camera 1000 is aligned with the fundus oculi Ef (that is, the optical system is moved in the x-direction, the y-direction, and the z-direction shown in FIG. 12 to be placed at a position appropriate for imaging) before imaging the fundus oculi Ef of the eye E. The optical system of the fundus camera 1000 is provided with an illumination optical system 100 to light the fundus oculi Ef of an eye E, an imaging optical system 120 to guide the fundus reflection light of the illumination light to the eyepiece part 8b, the still camera 9 and the imaging device 10.

The illumination optical system 100 comprises: an observation light source 101; a condenser lens 102; an imaging light source 103; a condenser lens 104; exciter filters 105 and 106; a ring transparent plate 107; a mirror 108; a liquid crystal display (LCD) 109; an illumination diaphragm 110; a relay lens 111; an aperture mirror 112; and an objective lens 113.

The observation light source 101 is composed of a halogen lamp, etc. and emits ambient light (continuous light) for observing the fundus oculi. The condenser lens 102 is an optical element for converging the ambient light (observation illumination light) emitted by the observation light source 101 and substantially evenly irradiating the observation illumination light to the fundus oculi.

The imaging light source 103 is composed of a xenon lamp, etc. to be flashed at the time of production of fundus oculi Ef images. The condenser lens 104 is an optical element for converging the flash light (imaging illumination light) emitted by the imaging light source 103 and irradiating the fundus oculi Ef evenly with the imaging illumination light.

The exciter filters 105 and 106 are filters used at the time of fluorography of images of a fundus oculi Ef. The exciter filters 105 and 106 can respectively be inserted into and removed from an optical path by a drive mechanism (not shown) such as a solenoid. The exciter filter 105 is placed on the optical path in the event of FAG (fluorescein angiography). Whereas, the exciter filter 106 is placed on the optical path in the event of ICG (indocyanine green angiography). Furthermore, when color images are to be obtained, both exciter filters 105 and 106 are retracted from the optical path.

The ring transparent plate 107 is placed in a conjugating location with a pupil of the eye E, and is equipped with a ring transparent part 107a taking an optical axis of the illumination optical system 100 as a center. The mirror 108 reflects the illumination light emitted by the observation light source 101 or by the imaging light source 103, in the direction of the optical axis of the imaging optical system 120. The LCD 109 displays a fixation target (not illustrated) for fixing the eye E.

The illumination diaphragm 110 is a diaphragm member to shut out part of the illumination light in order to prevent flare, etc. This illumination diaphragm 110 is composed so as to be movable in the light axial direction of the illumination optical system 100, and is thus capable of changing an illumination region of the fundus oculi Ef.

The aperture mirror 112 is an optical element to combine an optical axis of the illumination optical system 100 and an optical axis of the imaging optical system 120. In the center region of the aperture mirror 112, an aperture 112a is opened. The optical axis of the illumination optical system 100 and the optical axis of the imaging optical system 120 cross each other at a substantially central location of this aperture 112a. The objective lens 113 is installed in the objective lens part 8a of the main body part 8.

The illumination optical system 100 having such a composition illuminates the fundus oculi Ef in the following manner. First, at the time of fundus observation, the observation light source 101 is turned on and the observation illumination light is emitted. This observation illumination light is applied to the ring transparent plate 107 through the condenser lenses 102 and 104. (The exciter filters 105 and 106 are removed from the optical path.) The light passed through the ring transparent part 107a of the ring transparent plate 107 is reflected by the mirror 108, and after passing through the LCD 109, the illumination diaphragm 110 and the relay lens 111, reflected by the aperture mirror 112. The observing illumination light reflected by the aperture mirror 112 advances in the optical axial direction of the imaging optical system 120, and is converged by the objective lens 113 to enter the eye E, thereby illuminating the fundus oculi Ef.

At this moment, the ring transparent plate 107 is placed in a conjugating location with the pupil of the eye E and, on the pupil, a ring-shaped image of the observation illumination light entering the eye E is formed. The fundus reflection light of the observation illumination light is to be emitted from the eye E through a central dark part of the ring-shaped image on the pupil. Thus, an effect of observing illumination light entering the eye E on the fundus reflection light of the observing illumination light is prevented.

On the other hand, at the time of imaging of the fundus oculi Ef, flush light is emitted from the imaging light source 103 and the imaging illumination light is applied to the fundus oculi Ef through the same path. In the event of photofluo-graphing, either the exciter filter 105 or the exciter filter 106 is placed selectively on the optical path, depending on whether FAG imaging or ICG imaging is carried out.

Next, the imaging optical system 120 will be described. The imaging optical system 120 comprises: an objective lens 113; an aperture mirror 112 (an aperture 112a thereof); an imaging diaphragm 121; barrier filters 122 and 123; a variable magnifying lens 124; a relay lens 125; an imaging lens 126; a quick return mirror 127; and an imaging media 9a. Herein, the imaging media 9a is any imaging media (an image pick-up element such as CCD, a camera film, an instant film, etc.) used for the still camera 9.

The fundus reflection light of the illumination light, exiting from the eye E through the central dark part of the ring-shaped image formed on the pupil, enters the imaging diaphragm 121 through the aperture 112a of the aperture mirror 112. The aperture mirror 112 reflects cornea reflection light of the illumination light, and acts so as not to mix the cornea reflection light into the fundus reflection light entering the imaging diaphragm 121. As a result, generation of flare on the observation images and/or produced images is prevented.

The imaging diaphragm 121 is a plate-shaped member having a plurality of circular light transparent parts of different sizes. The plurality of light transparent parts compose diaphragms with different diaphragm values (F value), and are placed alternatively on the optical path by a drive mechanism (not illustrated herein).

The barrier filters 122 and 123 can be inserted into and removed from the optical path by a drive mechanism (not illustrated) such as a solenoid. In the event of FAG imaging, the barrier filter 122 is placed on the optical path, whereas in the event of ICG imaging, the barrier filter 123 is placed on the optical path. Furthermore, at the time of production of color images, both the barrier filters 122 and 123 are retracted from the optical path.

The variable magnifying lens 124 is movable in the light axial direction of the imaging optical system 120 by a drive mechanism (not illustrated herein). This makes it possible to change the magnifying ratio of an observation and the magnifying ratio in imaging, and to focus images of a fundus oculi. The imaging lens 126 is a lens to focus the fundus reflection light from the eye E onto the imaging media 9a.

The quick return mirror 127 is disposed rotatably around a rotary shaft 127a by a drive mechanism not illustrated herein. In the event of imaging a fundus oculi Ef with the still camera 9, the fundus reflection light is guided to the imaging media 9a by springing up the quick return mirror 127 obliquely mounted on the optical path. Whereas, in the event of imaging a fundus oculi with the imaging device 10 or of observing the fundus oculi with the naked eye of the examiner, the quick return mirror 127 is obliquely mounted on the optical path to upwardly reflect the fundus reflection light.

The imaging optical system 120 is further provided, for guiding the fundus reflection light reflected by the quick return mirror 127, with a field lens 128, a switching mirror 129, an eyepiece 130, a relay lens 131, a reflection mirror 132, an imaging lens 133, and an image pick-up element 10a. The image pick-up element 10a is an image pick-up element such as CCD installed internally in the imaging device 10. On the touch panel monitor 11 a fundus oculi image Ef' imaged by the image pick-up element 10a is displayed.

The switching mirror 129 is rotatable around a rotary shaft 129a, as well as the quick return mirror 127. This switching mirror 129 is obliquely disposed on the optical path during observation with the naked eye, and reflects the fundus reflection light to the eyepiece 130.

Also, when a fundus image is formed by using the imaging device 10, the switching mirror 129 is retracted from the optical path, and the fundus reflection light is guided toward the image pick-up element 10a. In this case, the fundus reflection light is directed toward the relay lens 131, reflected by the mirror 132, and focused onto the image pick-up element 10a by the imaging lens 133.

The fundus camera 1000 is a fundus observation device used for observing the state of the surface of a fundus oculi Ef, that is, the retina. In other words, the fundus camera 1000 is a device to obtain a 2-dimensional fundus oculi image when it sees the fundus oculi Ef from a direction of the corneal on the eye E. On the other hand, in the deep layer of retina tissues such as the choroidea or sclera exist, and a technology for observing these deep layer tissues has been desired. In recent years, devices for observing these deep layer tissues have been practically implemented (e.g. JP Patent laid-open No. 2003-00543, JP Patent laid-open No. 2005-241464).

The fundus observation devices disclosed in JP Patent laid-open No. 2003-00543 and JP Patent laid-open No. 2005-241464 are devices (referred to as an optical image measurement device, an optical coherence tomography device, and the like) to which so-called OCT (Optical Coherence Tomography) technology is applied. Such a fundus observation device is a device splitting low coherence light into two, guiding one of the lights (signal light) to a fundus oculi and the other (reference light) to a given reference object, and detecting and analyzing interference light obtained by overlaying the signal light through the fundus oculi and the reference light through the reference object, thereby forming tomographic images of the surface and deep layer tissue of the fundus oculi. Further, the optical measuring device is capable of forming a 3-dimensional image of the fundus oculi based on a plurality of tomographic images. These devices are generally called a Fourier domain OCT.

The Fourier domain OCT is designed to scan the signal light to irradiate the fundus oculi, thereby form a tomographic image having a depth-wise (z-direction shown in FIG. 12) cross section along a scanning line. Such scanning of the signal light is referred to as a B-scan (see NEDO Workshop "Seeing (examining) inside the body from the 'window' of the human body, the fundus oculi"—Development of an ultra early diagnostic device for lifestyle-related diseases using the latest optical technologies (held on Apr. 25, 2005), Internet, URL: http://www.nedo.go.jp/informations/koubo/170627_2/besshi3.pdf>).

When forming a 3-dimensional image, the Fourier domain OCT performs the B-scan along a plurality of scanning lines, and applies an interpolation process to the plurality of tomographic images obtained by the B-scan, thereby generating 3-dimensional image data. This 3-dimensional image data is referred to as volume data, voxel data or the like, as well as in a medical imaging diagnosis device such as an X-ray CT device. The 3-dimensional image data is image data in a form in which pixel data (e.g. luminance value and RGB value regarding brightness, contrasting density and color) is assigned to each of voxels arranged 3-dimensionally. A 3-dimensional image is displayed as a pseudo 3-dimensional image seen from a certain viewing angle obtained by rendering volume data.

Not only in opthalmology but generally in the medical field, an identical site of a patient is observed multiple times (hereinafter, may be referred to as "course observation or the like"), for example, in therapeutic course observation or preoperative and postoperative observation.

In the course observation or the like of the fundus oculi, in order to observe a noted site on the fundus oculi, such as the macular area, optic papilla and a detached site of retina, multiple times, it is necessary to specify the position of the noted site and capture an image at each observation time.

Regarding a site that is a landmark on the fundus oculi, such as optic papilla, it is easy to specify the position thereof. However, there exists a noted site whose position is difficult to specify simply by observing the image. Particularly, when the noted site exists in a deep layer (such as choroid membrane and sclera) of the fundus oculi, it is more difficult to specify the position of the noted site than when the noted site exists on the surface of the fundus oculi.

In addition, in the course observation or the like, it is preferable to photograph images at each time under the same conditions. For example, in an optical image measuring device, it is desired that various conditions such as the fixation position of an eye and a scan of signal lights (scanning position or scanning pattern) are the same.

However, it is very troublesome to specify the position of a noted site for each photograph and to manually input various conditions. In addition, an inadvertent mistake may intervene, such as forgetting to record the position of a noted site and photographing conditions, or making a mistake in setting the position or conditions.

SUMMARY OF THE INVENTION

In one aspect of the present invention, a fundus observation device comprises: an image forming part comprising a first image forming part and a second image forming part, the first image forming part forming a 2-dimensional surface image of fundus oculi of an eye through optical processing, the second image forming part optically scanning a surface region of the fundus oculi corresponding to at least a part of the 2-dimensional surface image to form a tomographic image of the fundus oculi; a controller configured to control the image forming part; and a storage configured to store control information including control instructions to be sent from the controller to the image forming part, when one of the 2-dimensional surface image and the tomographic image is formed, wherein the controller, at the time of formation of new one of the 2-dimensional surface image and the tomographic image, instructs the image forming part to form the new one of the 2-dimensional surface image and the tomographic image based on the control information stored in the storage.

In another aspect of the present invention, a computer readable medium has computer readable code embodied therein for causing a computer system to perform a predetermined process, the computer having: a controller configured to control an image forming part; and a storage, the image forming part comprising a first image forming part and a second image forming part, the first image forming part forming a 2-dimensional surface image of fundus oculi of an eye through optical processing, the second image forming part optically scanning a surface region of the fundus oculi corresponding to at least a part of the 2-dimensional surface image to form a tomographic image of the fundus oculi, wherein the predetermined process comprising: storing control information in a storage, the control information including control instructions to be sent from the controller to the image forming part, when one of the 2-dimensional surface image and the tomographic image is formed; and controlling the image forming part, at the time of formation of new one of the 2-dimensional surface image and the tomographic image, based on the control information.

BRIEF DESCRIPTION OF THE DRAWINGS

FIG. 8 is a schematic diagram showing one example of the feature of scan of signal light in the preferred embodiment of the fundus observation device according to the present invention.

DETAILED DESCRIPTION OF THE REFERENCE EMBODIMENTS

Figure 1:
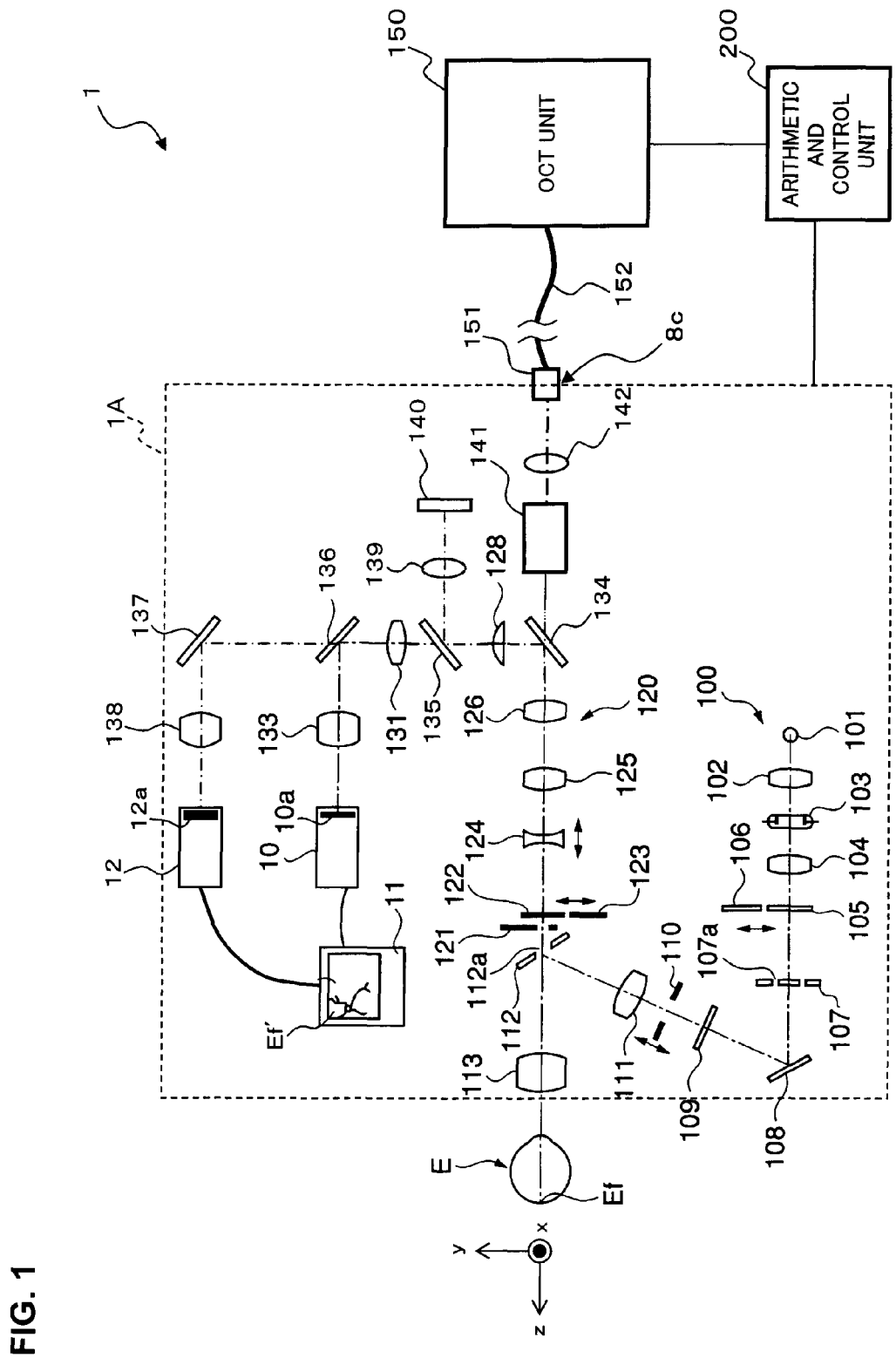
FIG. 1 is a schematic diagram showing one example of the entire constitution in a preferred embodiment of the fundus observation device according to the present invention.

One example of preferable embodiments of a fundus observation device and a program controlling the same according to the present invention will be described in detail referring to the drawings. For the same structural parts as conventional ones, the same symbols used in FIG. 11 and FIG. 12 will be used.

Figure 2:
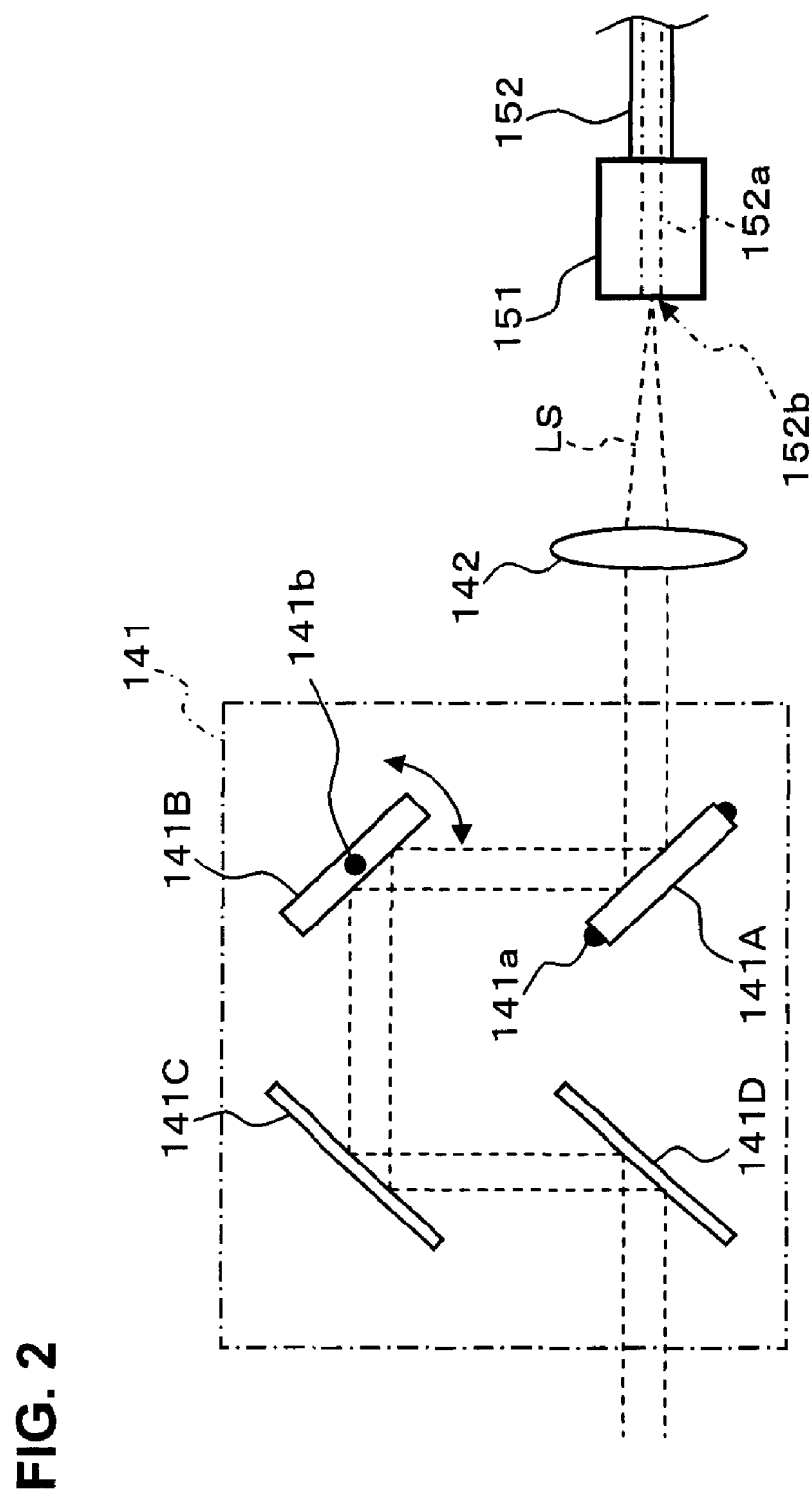
FIG. 2 is a schematic diagram showing one example of the constitution of a scanning unit installed in the fundus camera unit in the preferred embodiment of the fundus observation device according to the present invention.
Figure 3:
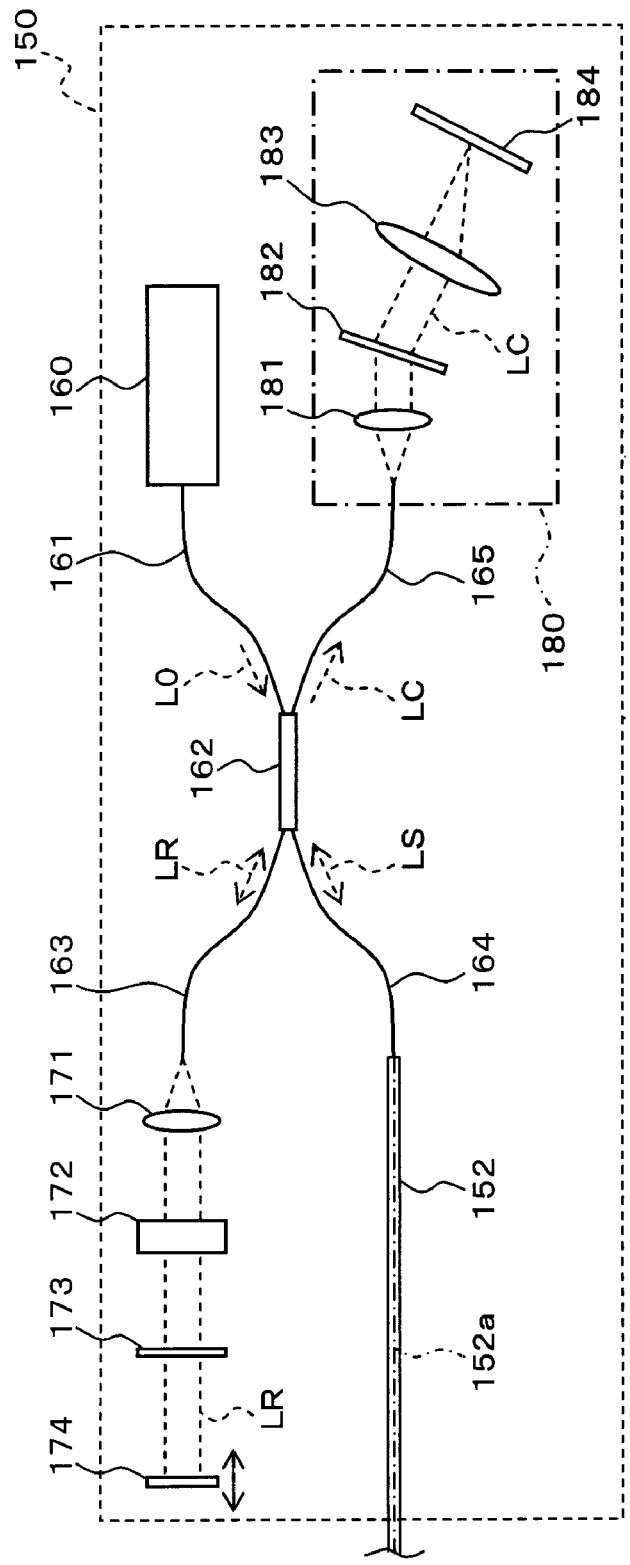
FIG. 3 is a schematic diagram showing one example of the constitution of an OCT unit in the preferred embodiment of the fundus observation device according to the present invention.
Figure 4:
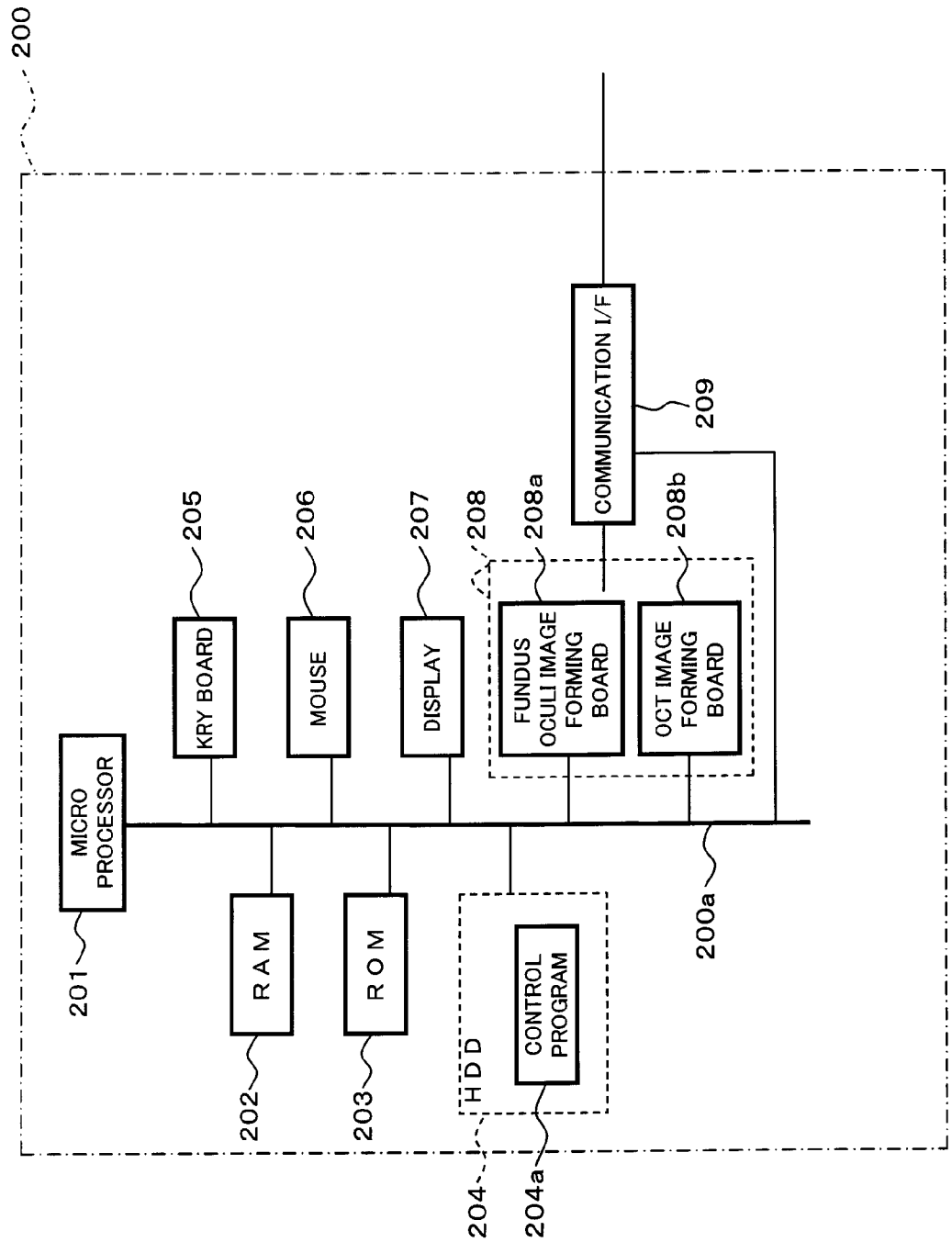
FIG. 4 is a schematic block diagram showing one example of the hardware configuration of an arithmetic and control unit in the preferred embodiment of the fundus observation device according to the present invention.
Figure 5:
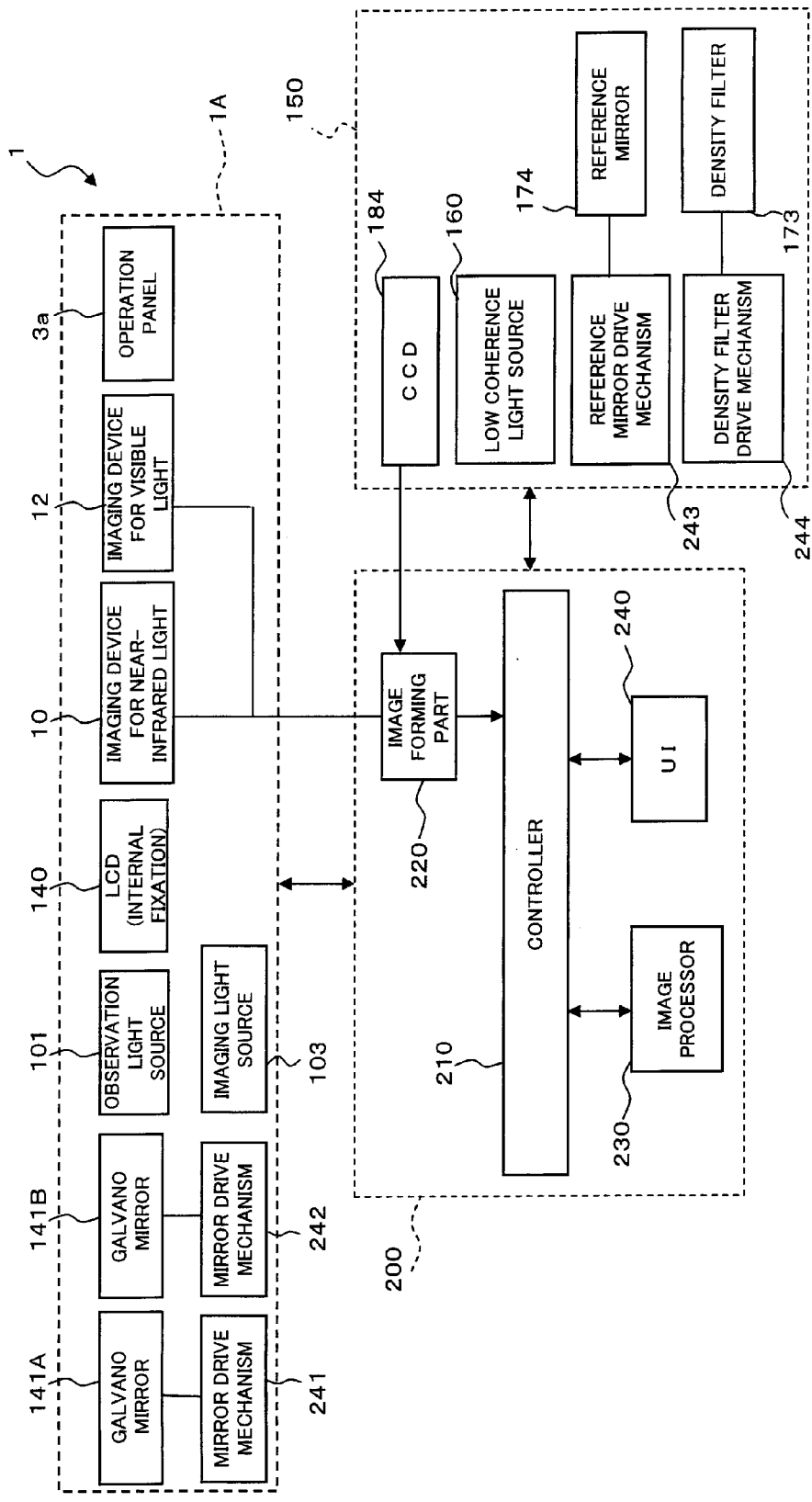
FIG. 5 is a schematic block diagram showing one example of the constitution of a control system in the preferred embodiment of the fundus observation device according to the present invention.
Figure 6:
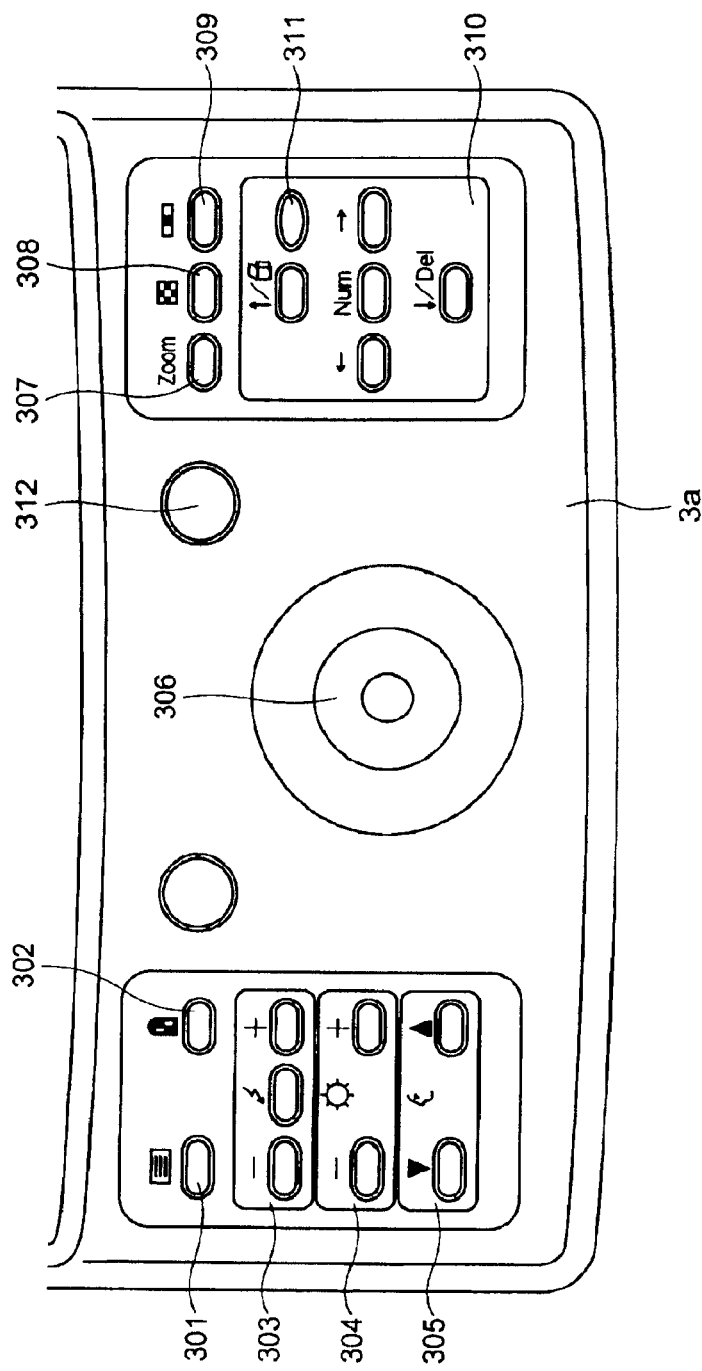
FIG. 6 is a schematic diagram showing an example of the appearance of an operation panel in the preferred embodiment of the fundus observation device according to the present invention.
Figure 7:
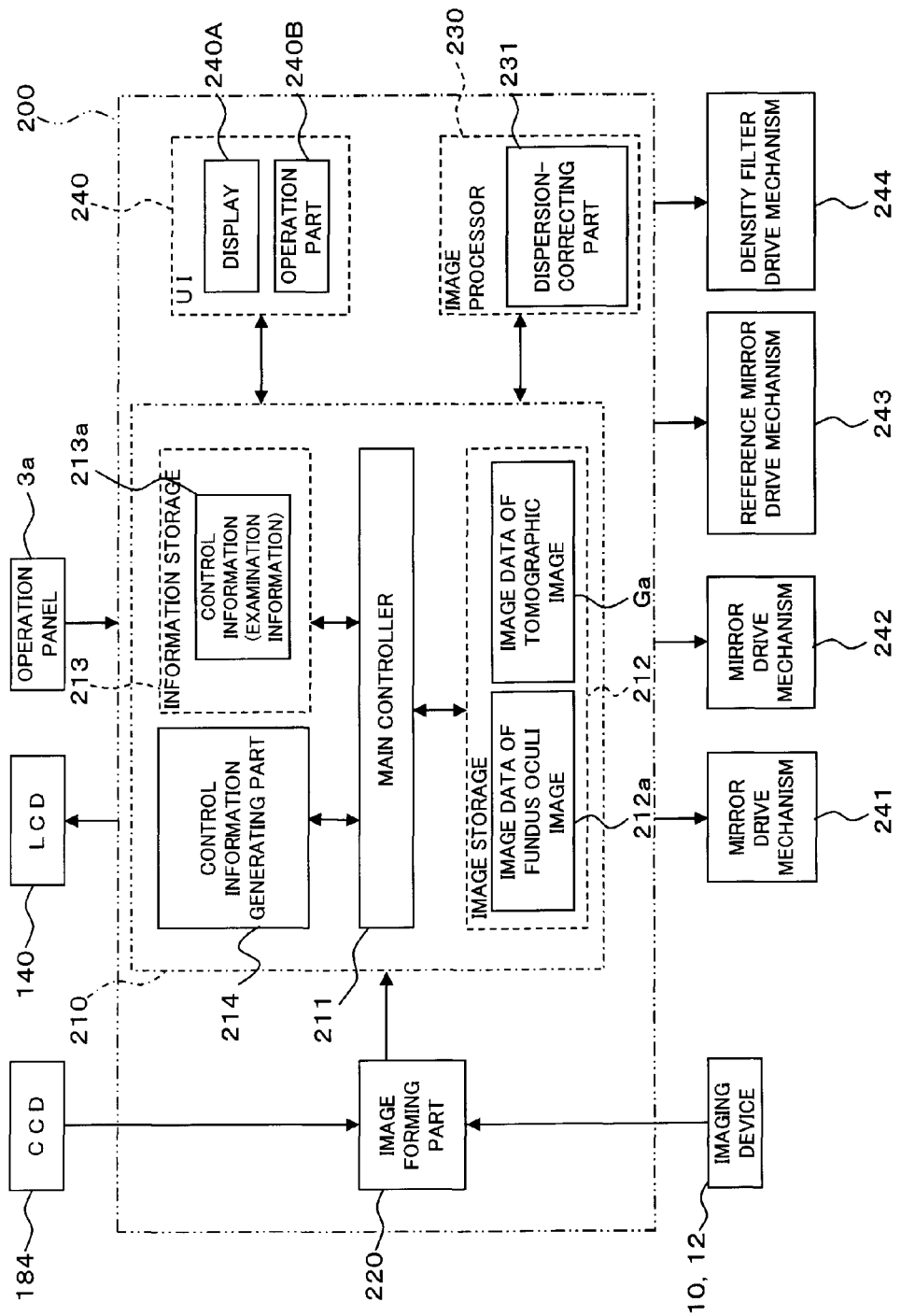
FIG. 7 is a drawing showing one example of the functional configuration of an arithmetic and control unit in the preferred embodiment of the fundus observation device according to the present invention.

First, referring to FIGS. 1 through 7, the constitution of the fundus observation device according to the present invention will be described. FIG. 1 shows one example of the entire constitution of a fundus observation device 1 according to the present embodiment. FIG. 2 shows one example of the constitution of a scanning unit 141 in a fundus camera unit 1A. FIG. 3 shows one example of the constitution of an OCT unit 150. FIG. 4 shows a hardware configuration of an arithmetic and control unit 200. FIG. 5 shows one example of the configuration of a control system of the fundus observation device 1. FIG. 6 shows one example of the constitution of an operation panel 3a disposed to the fundus camera unit 1A. FIG. 7 shows one example of the configuration of a control system of the arithmetic and control unit 200.

The Entire Configuration

As shown in FIG. 1, the fundus observation device 1 according to the present embodiment comprises the fundus camera unit 1A that functions as a fundus camera, an OCT unit 150 accommodating an optical system of an optical image measuring device (OCT device), and the arithmetic and control unit 200 that executes various arithmetic processes, control processes, etc.

To the OCT unit 150, one end of a connection line 152 is attached. To the other end of this connection line 152, a connector part 151 is attached. This connector part 151 is mounted to a mounting part 8c shown in FIG. 11. Furthermore, a conductive optical fiber runs through the inside of the connection line 152. The OCT unit 150 and the fundus camera unit 1A are optically connected through the connection line 152. The constitution details of the OCT unit 150 will be described later referring to FIG. 3.

Configuration of Fundus Camera Unit

The fundus camera unit 1A is a device configured to form a 2-dimensional image of the surface of a fundus oculi of an eye based on optically obtained data (data detected by imaging devices 10 and 12). The fundus camera unit 1A has substantially the same appearance as the conventional fundus camera 1000 shown in FIG. 11. Furthermore, as in the conventional optical system shown in FIG. 12, the fundus camera unit 1A is provided with an illumination optical system 100 lighting a fundus oculi Ef of an eye E, and an imaging optical system 120 guiding the fundus reflection light of the illumination light to the imaging device 10.

Although the details will be described later, the imaging device 10 in the imaging optical system 120 of the present embodiment is used for detecting the illumination light having a wavelength in the near-infrared region. Furthermore, in this imaging optical system 120, the imaging device 12 detecting the illumination light having a wavelength in the visible region is provided separately. In addition, this imaging optical system 120 guides the signal light from the OCT unit 150 to the fundus oculi Ef, and guides the signal light through the fundus oculi Ef to the OCT unit 150.

As well as the conventional ones, the illumination optical system 100 comprises an observation light source 101, a condenser lens 102, an imaging light source 103, a condenser lens 104, exciter filters 105 and 106, a ring transparent plate 107, a mirror 108, an LCD 109, an illumination diaphragm 110, a relay lens 111, an aperture mirror 112, and an objective lens 113.

The observation light source 101 emits the illumination light of a wavelength in the visible region included within, for example, about 400 nm to 700 nm. Furthermore, the imaging light source 103 emits the illumination light of a wavelength in the near-infrared region included within, for example, about 700 nm to 800 nm. The near-infrared light emitted from this imaging light source 103 is provided shorter than the wavelength of the light used by the OCT unit 150 (described later).

The imaging optical system 120 comprises the objective lens 113, the aperture mirror 112 (an aperture 112a thereof), an imaging diaphragm 121, barrier filters 122 and 123, a variable magnifying lens 124, a relay lens 125, an imaging lens 126, a dichroic mirror 134, a field lens 128, a half mirror 135, a relay lens 131, a dichroic mirror 136, an imaging lens 133, the imaging device 10 (an image pick-up element 10a), a reflection mirror 137, an imaging lens 138, the imaging device 12 (an image pick-up element 12a), a lens 139, and an LCD (Liquid crystal Display) 140.

Figure 12:
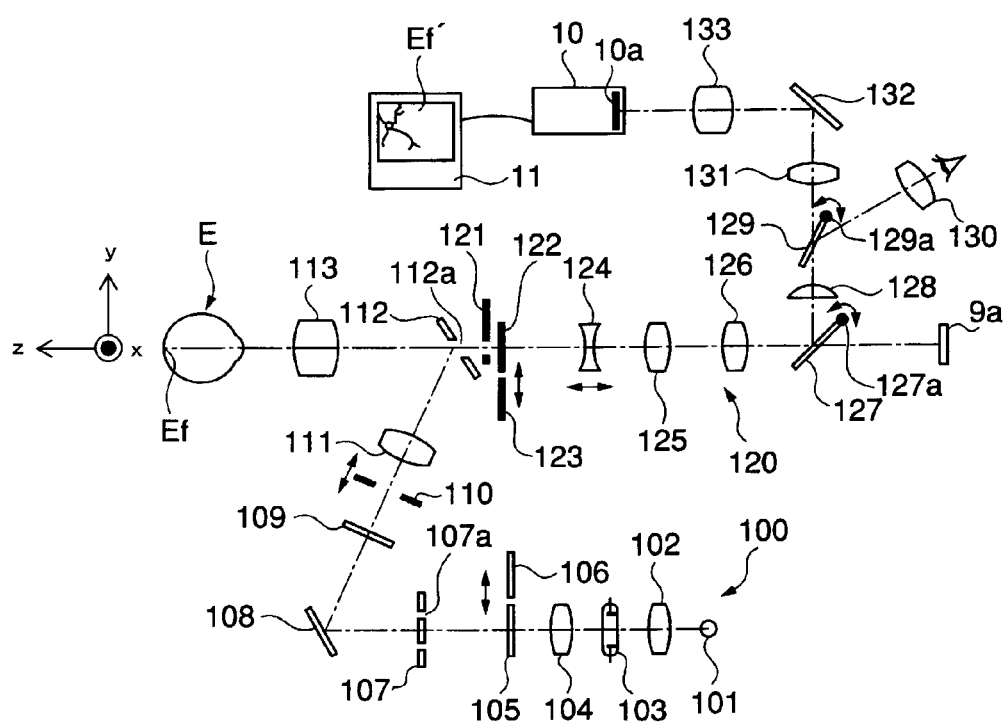
FIG. 12 is a schematic diagram showing one example of the internal constitution (optical system constitution) of a conventional fundus observation device (fundus camera).

The imaging optical system 120 according to the present embodiment is different from the conventional imaging optical system 120 shown in FIG. 12 in that the dichroic mirror 134, the half mirror 135, the dichroic mirror 136, the reflection mirror 137, the imaging lens 138, the lens 139 and the LCD 140 are provided.

The dichroic mirror 134 reflects the fundus reflection light (having a wavelength included within a range of about 400 nm to 800 nm) of the illumination light from the illumination optical system 100, and transmits a signal light LS (having a wavelength included within a range of, for example, about 800 nm to 900 nm; described later) from the OCT unit 150.

Furthermore, the dichroic mirror 136 transmits the illumination light having a wavelength in the visible region from the illumination optical system 100 (visible light of a wavelength within about 400 nm to 700 nm emitted from the observation light source 101) and reflects the illumination light having a wavelength in the near-infrared region (near-infrared light of a wavelength within about 700 nm to 800 nm emitted from the imaging light source 103).

On the LCD 140, a fixation target (internal fixation target), etc. for fixing the eye E is displayed. The light from this LCD 140 is reflected by the half mirror 135 after being converged by the lens 139, and is reflected by the dichroic mirror 136 through the field lens 128. Further, it passes through the imaging lens 126, the relay lens 125, the variable magnifying lens 124, the aperture mirror 112 (aperture 112a thereof), the objective lens 113, etc. and enters the eye E. As a result, an internal fixation target, etc. is displayed in the fundus oculi Ef of an eye E.

The LCD 140 functions as one example of the "fixation target display" according to the present invention. In addition, the above group of optical elements for projecting the displayed fixation target onto the eye E functions as one example of the "projection optical system" according to the present invention. Moreover, the LCD 140 and the above group of optical elements are equivalent to one example of the "fixation target projector" according to the present invention.

The image pick-up element 10a is an image pick-up element such as CCD and CMOS installed internally in the imaging device 10 such as a TV camera, and is particularly used for detecting light of a wavelength in the near-infrared region (that is, the imaging device 10 is an infrared TV camera for detecting near-infrared light). The imaging device 10 outputs a video signal as a result of detection of near-infrared light.

A touch panel monitor 11 displays a 2-dimensional image (fundus image Ef') of the surface of the fundus oculi Ef based on this video signal. Also, this video signal is sent to the arithmetic and control unit 200, and the fundus oculi image is displayed on the display (described later).

Furthermore, when the fundus oculi is imaged by the imaging device 10, for example, the illumination light emitted from the imaging light source 103 of the illumination optical system 100 and having a wavelength in the near-infrared region may be used.

On the other hand, the image pick-up element 12a is an image pick-up element such as CCD and CMOS installed internally in the imaging device 12 such as a TV camera, and is particularly used for detecting light of a wavelength in the visible region (that is, the imaging device 12 is a TV camera for detecting visible light). The imaging device 12 outputs a video signal as a result of detection og visible light.

A touch panel monitor 11 displays a 2-dimensional image (fundus image Ef') of the surface of the fundus oculi Ef based on this video signal. Also, this video signal is sent to the arithmetic and control unit 200, and the fundus oculi image is displayed on a display (to be described later).

When the fundus oculi are being imaged by this imaging device 12, for example, the illumination light emitted from the observation light source 101 of the illumination optical system 100, having a wavelength in the visible region may be used.

The imaging optical system 120 according to the present embodiment is provided with a scanning unit 141 and a lens 142. The scanning unit 141 is equipped with a constitution to scan the light (signal light LS; described later) emitted from the OCT unit 150 on the fundus oculi Ef, and functions as one example of the "scanner" according to the present invention.

The lens 142 makes the signal light LS guided from the OCT unit 150 through the connection line 152 enter the scanning unit 141 in the form of a parallel light flux. Furthermore, the lens 142 acts so as to converge the fundus reflection light of the signal light LS having reached through the scanning unit 141.

FIG. 2 shows one example of the concrete constitution of the scanning unit 141. The scanning unit 141 comprises galvanometer-mirrors 141A, 141B, and reflection mirrors 141C, 141D.

The galvanometer-mirrors 141A and 141B are reflection mirrors disposed so as to be rotatable about rotary shafts 141a and 141b, respectively. The galvanometer-mirrors 141A and 141B are rotated about the rotary shafts 141a and 141b, respectively, by a drive mechanism described later (mirror drive mechanisms 241 and 242 shown in FIG. 5), whereby the orientations of reflection surfaces thereof (faces reflecting the signal light LS), namely, the positions of the Galvano mirrors 141A and 141B are changed, respectively. The "galvanometer-mirrors" of the present embodiment each include the galvanometer-mirrors 141A and 141B (reflection mirrors) and the mirror drive mechanisms 241 and 242.

The rotary shaft 141a and 141b are arranged perpendicular to each other. In FIG. 2, the rotary shaft 141a of the galvanometer-mirror 141A is arranged in parallel to the paper face, while the rotary shaft 141b of the galvanometer-mirror 141B is arranged perpendicular to the paper face.

That is, the galvanometer-mirror 141B is formed so as to be rotatable in the directions indicated by an arrow pointing in both directions in FIG. 2, while the galvanometer-mirror 141A is formed so as to be rotatable in the directions perpendicular to the arrow pointing in both the directions. As a result, this pair of galvanometer-mirrors 141A and 141B act so that the reflecting direction of the signal light LS changes to directions perpendicular to each other. As can be seen from FIG. 1 and FIG. 2, the signal light LS will be scanned in the x-direction when the galvanometer-mirror 141A is turned, and the signal light LS will be scanned in the y-direction when the galvanometer-mirror 141B is turned.

The signal lights LS reflected by the Galvano mirrors 141A and 141B are reflected by mirrors 141C and 141D, thereby advancing in the same direction as having entered into the Galvano mirror 141A.

As described previously, a conductive optical fiber 152a runs inside the connection line 152, and an end face 152b of the optical fiber 152a is arranged opposite to the lens 142. The signal light LS emitted from this end face 152b advances while gradually expanding its beam diameter toward the lens 142 until being converged to a parallel light flux by this lens 142. On the contrary, the fundus reflection light of the signal light LS is converged toward the end face 152b by this lens 142.

Configuration of OCT Unit

Next, the configuration of the OCT unit 150 will be described referring to FIG. 3. The OCT unit 150 shown in FIG. 3 is a device configured to form a tomographic image of fundus oculi based on data obtained by an optical scan (data detected by CCD 184 described below).

The OCT unit 150 has a similar optical system to the conventional optical image measuring device. That is, the OCT unit 150 has an interferometer that splits the light emitted from a light source into a reference light and a signal light, and generates interference light by superposing the reference light through the reference object and the signal light from an object to be measured (fundus oculi Ef), and a part configured to output a signal (detection signal) as a result of detecting the interference light toward the arithmetic and control unit 200. The arithmetic and control unit 200 forms a tomographic image of the object to be measured (fundus oculi Ef) by analyzing this signal.

A low coherence light source 160 is composed of a broad band light source such as super luminescent diode (SLD) or a light emitting diode (LED) that emits low coherence light L0. This low coherence light L0, for instance, has a wavelength in the near-infrared region and is supposed to be light having a time-wise coherence length of approximately several tens of micro-meters.

The low coherence light L0 emitted from the low coherence light source 160 has a longer wavelength than the illumination light (wavelength: about 400 nm to 800 nm) of the fundus camera unit 1A, for example, a wavelength included within about 800 nm to 900 nm. This low coherence light source 160 corresponds to one example of the "light source" according to the present invention.

The low coherence light L0 emitted from the low coherence light source 160 is guided to an optical coupler 162 through an optical fiber 161 composed of, e.g. a single mode fiber, or PM (Polarization maintaining) fiber, and then split into reference light LR and signal light LS.

Furthermore, the optical coupler 162 has both actions, i.e. a part (splitter) for splitting lights, and a part (coupler) superposing lights); however, herein conventionally referred to as an "optical coupler".

The reference light LR generated by the optical coupler 162 is guided by an optical fiber 163 composed of a single mode fiber or the like, and emitted from the end face of the fiber. The emitted reference light LR is made by a reference mirror 174 (reference object) through a glass block 172 and a density filter 173 after having been converged into a parallel light flux by a collimator lens 171.

The reference light LR reflected by the reference mirror 174 is converged to the end face of the optical fiber 163 by the collimator lens 171 again through the density filter 173 and the glass block 172. The converged reference light LR is guided to the optical coupler 162 through the optical fiber 163.

The glass block 172 and the density filter 173 act as a delaying part for matching the optical path length (optical distance) between the reference light LR and the signal light LS, and as a dispersion correction part for matching the dispersion characteristics of the reference light LR and the signal light LS.

In addition, the density filter 173 also acts as a dark filter for reducing the amount of the reference light, and is composed of a rotating ND (neutral density) filter, for example. This density filter 173 acts to change the reduction amount of the reference light LR by being rotary driven by a drive mechanism including a drive unit such as a motor (density filter drive mechanism 244 described later; refer to FIG. 5). That makes it possible to change the amount of the reference light LR contributing to generation of the interference light LC.

This density filter 173 functions as one example of the "filter" according to the present invention. In addition, the density filter drive mechanism 244 functions as one example of the "filter drive mechanism" according to the present invention.

Furthermore, the reference mirror 174 is provided to be movable in a propagating direction (direction of arrow shown in FIG. 3) of the reference light LR. As a result, the light path length of the reference light LR according to the axial length of the eye E, etc. is ensured. Moreover, the reference mirror 174 is operated to move by a drive mechanism (reference mirror driving mechanism 243 described later; refer to FIG. 5) including a driving part such as a motor.

Whereas, the signal light LS generated by the optical coupler 162 is guided to the end of the connection line 152 through an optical fiber 164 composed of a single mode fiber or the like. The conductive optical fiber 152a runs inside the connection line 152. Herein, the optical fiber 164 and the optical fiber 152a may be composed of a single optical fiber, or may be jointly formed by connecting the end faces of the respective fibers. In either case, it is sufficient as long as the optical fiber 164 and 152a are composed so as to be capable of transferring the signal light LS between the fundus camera unit 1A and the OCT unit 150.

The signal light LS is guided within the connection line 152 to the fundus camera unit 1A. Then, the signal light LS enters into the eye E through the lens 142, the scanning unit 141, the dichroic mirror 134, the imaging lens 126, the relay lens 125, the variable magnifying lens 124, the imaging diaphragm 121, the aperture 112a of the aperture mirror 112, and the objective lens 113 (the barrier filter 122 and 123 are retracted from the optical path, respectively, when the signal light LS is made to enter the eye E).

The signal light LS having entered into the eye E forms an image on the fundus oculi (retina) Ef and is then reflected. At this moment, the signal light LS is not only reflected on the surface of the fundus oculi Ef, but also scattered at the refractive index boundary after reaching the deep area of the fundus oculi Ef. As a result, the signal light LS from the fundus oculi Ef becomes a light containing information reflecting the surface state of the fundus oculi Ef and information reflecting the scattered state in the rear at the refractive index boundary of the deep area tissue. The light may be simply referred to as "fundus reflection light of the signal light LS.

The fundus reflection light of the signal light LS advances reversely on the above path within the fundus camera unit 1A and converges at the end face 152b of the optical fiber 152a, then enters into the OCT unit 150 through the optical fiber 152a, and returns to the optical coupler 162 through the optical fiber 164.

The optical coupler 162 overlays this signal light LS returning through the fundus oculi Ef on the reference light LR reflected at the reference mirror 174, thereby generating the interference light LC. The generated interference light LC is guided into a spectrometer 180 through an optical fiber 165 composed of a single mode fiber or the like.

Herein, the "interference optical generator" according to the present invention is composed of an interferometer including at least an optical coupler 162, optical fibers 163 and 164, and a reference mirror 174. Although a Michelson-type interferometer is adopted in the present embodiment, for instance, a Mach Zender type, etc. and any type of interferometer may be adopted appropriately.

The spectrometer 180 comprises a collimator lens 181, a diffraction grating 182, an image forming lens 183, and a CCD (Charge Coupled Device) 184. The diffraction grating 182 in the present embodiment is a transmission-type diffraction grating; however, needless to say, a reflection-type diffraction grating may also be used. Furthermore, needless to say, it is also possible to adopt, in place of the CCD 184, other photo-detecting elements. This photo-detecting element is one example of the "detector" according to the present invention.

The interference light LC having entered the spectrometer 180 is split (resolved into spectra) by the diffraction grating 182 after having been converged into a parallel light flux by the collimator lens. The split interference light LC forms an image on the image pick-up surface of the CCD 184 by the image forming lens 183. The CCD 184 receives the interference light LC and converts to an electrical detection signal, and outputs the detection signal to the arithmetic and control unit 200.

Configuration of Arithmetic and Control Unit

Next, the configuration of the arithmetic and control unit 200 will be described. This arithmetic and control unit 200 corresponds to one example of the "computer" according to the present invention.

This arithmetic and control unit 200 analyzes the detection signal input from the CCD 184 of the spectrometer 180 of the OCT unit 150, and performs a process of forming tomographic images of the fundus oculi Ef of the eye E. The analysis technique then is the same technique as the conventional Fourier domain OCT technique.

Also, the arithmetic and control unit 200 performs a process of forming (image data of) a 2-dimensional image showing the state of the surface of the fundus oculi Ef (retina) based on the video signals output from the imaging devices 10 and 12 of the fundus camera unit 1A.

Furthermore, the arithmetic and control unit 200 executes the control of each part of the fundus camera unit 1A and the control of each part of the OCT unit 150.

The control of the fundus camera unit 1A is, for example: control of emission of illumination light by the observation light source 101 or the imaging light source 103; control of insertion/retraction operation of the exciter filters 105 and 106 or the barrier filters 122 and 123 to/from the optical path; control of the operation of a display such as the liquid crystal display 140; control of shift of the illumination diaphragm 110 (control of the diaphragm value); control of the diaphragm value of the imaging diaphragm 121; control of shift of the variable magnifying lens 124 (control of the magnification), etc. Further, the arithmetic and control unit 200 performs control of the rotary operation of the Galvano mirrors 141A and 141B within the scanning unit 141 (control of the directions of the reflection faces).

Whereas, control of the OCT unit 150 is, for example: control of emission of the low coherence light by the low coherence light source 160; control of movement of the reference mirror 174; control of the rotary operation of the density filter 173 (operation of changing the reduction amount of the reference light LR); control of the accumulated time of the CCD 184, etc.

One example of the hardware configuration of the arithmetic and control unit 200 that acts as described above will be described referring to FIG. 4.

The arithmetic and control unit 200 is provided with a hardware configuration that is the same as conventional computers. To be specific, the arithmetic and control unit 200 comprises: a microprocessor 201 (CPU, MPU, etc.), a RAM 202, a ROM 203, a hard disk drive (HDD) 204, a keyboard 205, a mouse 206, a display 207, an image forming board 208, and a communication interface (I/F) 209. These parts are connected through a bus 200a.

In addition, the arithmetic and control unit 200 may comprise a reading device such as a card reader for reading recorded content of a patient's card on which patient information, including patient identification information such as a patient ID, is recorded. This card reader is used, for example, in a state connected to a connector such as a USB (Universal Serial Bus) port (not shown herein) of a computer forming the arithmetic and control unit 200. Such a reading device reading the patient identification information and inputting the same into the arithmetic and control unit 200 functions as one example of the "input part" according to the present invention.

The microprocessor 201 executes operations characteristic to the present embodiment by loading a control program 204a stored in the hard disk drive 204, onto the RAM 202. This control program 204a corresponds to one example of the "program controlling the fundus observation device" according to the present invention.

Furthermore, the microprocessor 201 executes control of each of the aforementioned parts of the device, various arithmetic processes, etc. Moreover, the microprocessor 201 executes control of each of the parts of the device responding to an operation signal from the keyboard 205 or the mouse 206, control of display processes by the display 207, control of transmitting/receiving processes of various types of data or control signals by the communication interface 209, etc. In addition, the microprocessor 201 has a function of providing date and time information, as usual.

The keyboard 205, the mouse 206 and the display 207 are used as a user interface of the fundus observation device 1. The keyboard 205 is used as a device for inputting letters, figures, etc. by typing, for example. The mouse 206 is used as a device for performing various input operations to the display screen of the display 207.

Furthermore, the display 207 may be any display device composed of LCD (Liquid Crystal Display), CRT (Cathode Ray Tube) or the like. The display 207 displays images of the fundus oculi Ef formed by the fundus observation device 1, and displays various operation screens, set-up screens, etc.

In addition, it can be configured so that it is possible to, by causing the display 207 to display a predetermined input screen and operating the keyboard 205 or the mouse 206, input the patient identification information to the input screen. In this case, the user interface is used as one example of the "input part" according to the present invention.

The user interface of the fundus observation device 1 is not limited to the above configuration but may be configured by using any user interfaces equipped with a function to display various information and a function to input various information, such as a track ball, a control lever, a touch panel type of LCD, and a control panel for opthalmology examinations.

An image forming board 208 is a dedicated electronic circuit for a process of forming (image data of) images of the fundus oculi Ef of the eye E. In this image forming board 208, a fundus image forming board 208a and an OCT image forming board 208b are installed.

The fundus image forming board 208a is a dedicated electronic circuit operating to form the image data of the fundus oculi image based on the video signals from the imaging device 10 and the imaging device 12 of the fundus camera unit 1A.

Furthermore, the OCT image forming board 208b is a dedicated electronic circuit operating to form image data of tomographic images of the fundus oculi Ef based on the detection signal from the CCD 184 of the spectrometer 180 in the OCT unit 150.

The image forming board 208 allows increase of the processing speed for forming image data of fundus images and tomographic images.

A communication interface 209 operates to send the control signal from the microprocessor 201 to the fundus camera unit 1A and OCT unit 150. Also, the communication interface 209 operates to receive the video signals from the imaging devices 10 and 12 of the fundus camera unit 1A and the detection signal from the CCD 184 of the OCT unit 150, and input the signals to the image forming board 208. At this time, the communication interface 209 operates to input the video signals from the imaging devices 10 and 12 to the fundus image forming board 208a, and input the detection signal from the CCD 184 to the OCT image forming board 208b.

Moreover, in a case where the arithmetic and control unit 200 is connected to a network such as LAN (Local Area Network) or Internet, the communication interface 209 may be configured, equipped with a network adapter such as LAN card or a communication equipment such as a modem, so as to be able to perform data communication through the network. In this case, by installing a server accommodating the control program 204a on the network, and at the same time, configuring the arithmetic and control unit 200 as a client terminal of the server, it is possible to cause the fundus observation device 1 to execute the operation according to the present invention.

Control System Configuration

The configuration of the control system of the fundus observation device 1 having the configuration described above will be described referring to FIG. 5 through FIG. 7. FIG. 5 shows a part related to the operations and processes according to the present embodiment, particularly selected from among constituents composing the fundus observation device 1. FIG. 6 shows one example of the constitution of an operation panel 3a disposed to the fundus camera unit 1A. FIG. 7 is a block diagram showing a detailed constitution of the arithmetic and control unit 200.

Controller

The control system of the fundus observation device 1 is configured mainly having a controller 210 of the arithmetic and control unit 200. The controller 210 comprises the microprocessor 201, the RAM202, the ROM203, the hard disk drive 204 (control program 204a), and the communication interface 209.

The controller 210 executes the controlling processes by the microprocessor 201 operating based on the control program 204a. In specific, for the fundus camera unit 1A, the controller 210 performs control of the mirror drive mechanisms 241 and 242 changing the positions of the galvanometer-mirrors 141A and 141B, and control of the display operation of the internal fixation target by the LCD 140, etc. For the OCT unit 150, the controller 210 performs control of the low coherence light source 160 and the CCD 184, control of the density filter drive mechanism 244 rotating the density filter 173, and control of the reference mirror drive mechanism 243 moving the reference mirror 174 along the traveling direction of the reference light LR, etc.

Furthermore, the controller 210 performs control for causing the display 207 of the user interface 240 to display two kinds of images produced by the fundus observation device 1: that is, a 2-dimensional image (fundus image Ef') of the surface of the fundus oculi Ef obtained by the fundus camera unit 1A, and a tomographic image of the fundus oculi Ef formed based on the detection signal obtained by the OCT unit 150. These images may also be displayed on the display 207, separately or simultaneously. The details of the constitution of the controller 210 will be described later referring to FIG. 7.

Image Forming Part

An image forming part 220 is configured to perform a process of forming image data of the fundus image based on the video signal from the imaging devices 10 and 12 of the fundus camera unit 1A and a process of forming image data of the tomographic images of the fundus oculi Ef based on the detection signal from the CCD 184 of the OCT unit 150. This imaging forming part 220 comprises the imaging forming board 208, and the communication interface 209. In this specification, "image" may be identified with "image data" corresponding thereto.

The "first image forming part" according to the present invention comprises, for example, each part of the fundus camera unit 1A for capturing a 2-dimensional image of the surface of the fundus oculi Ef and the image forming part 220 (fundus image forming board 208a). The "second image forming part" according to the present invention comprises, for example, each part of the fundus camera unit 1A for capturing a tomographic image of the fundus oculi Ef, the OCT unit 150, the image forming part 220 (OCT image forming board 208b), and an image processor 230. The "image forming part" according to the present invention comprises, for example, each part of the first image forming part, and each part of the second image forming part.

Image Processor

The image processor 230 applies various image processes to image data of the images formed by the image forming part 220. For example, it operates to perform a process of forming image data of a 3-dimensional image of the fundus oculi Ef based on the tomographic images of the fundus oculi Ef corresponding to the detection signal from the OCT unit 150, various correction processes such as brightness correction and dispersion correction of the images, etc.

Herein, image data of a 3-dimensional image is image data made by assigning pixel values to each of a plurality of voxels arranged 3-dimensionally, referred to as volume data, voxel data, and so forth. In the case of display of an image based on volume data, the image processor 230 operates to form image data of a pseudo 3-dimensional image seen from a particular viewing direction by applying a rendering process (such as volume rendering and MIP (Maximum Intensity Projection)) to the volume data. A display device such as the display device 207 displays such a pseudo 3-dimensional image based on the image data.

In addition, the image processor 230 executes a process of extracting an image region corresponding to each layer (such as retina) included in a tomographic image of the fundus oculi Ef or an image region corresponding to the boundary between layers, as in the conventionally one. Furthermore, it executes a process of calculating the thickness of the layer based on the extraction result.

The image processor 230 performing the processes described above comprises the microprocessor 201, the RAM 202, the ROM 203, and the hard disk drive 204 (control program 204a).

User Interface

The user interface (UI) 240, as shown in FIG. 7, comprises a display 240A composed of a display device such as the display 207, and an operation part 240B composed of an input device such as the keyboard 205 and an operation device such as the mouse 206. The operation part 240B functions as one example of "input part" according to the present invention, as well as the aforementioned reading device such as a card reader.

Operation Panel

Figure 11:
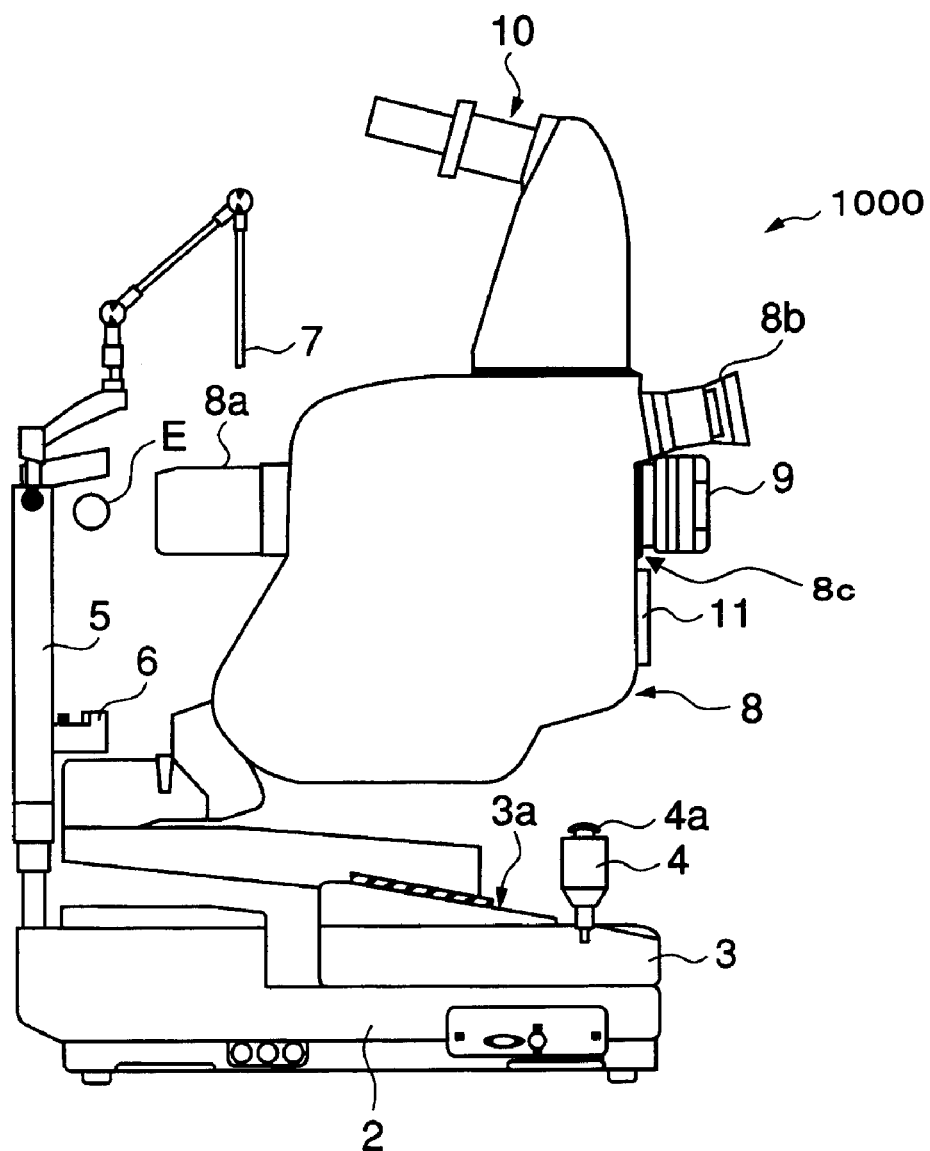
FIG. 11 is a schematic diagram showing one example of the appearance of a conventional fundus observation device (fundus camera).

The operation panel 3a of the fundus camera unit 1A will be described below. As shown in FIG. 11, this operation panel 3a is arranged, for example, on the platform 3 of the fundus camera unit 1A.

The operation panel 3a according to the present embodiment is different from the conventional configuration described above. It is provided with an operating part used to input an operation request for capturing a 2-dimensional image (fundus image Ef') of the surface of the fundus oculi Ef and an operating part used for an input operation for capturing a tomographic image of the fundus oculi Ef (traditionally, only the former operating part is provided).

In the present embodiment, placement of the operation panel 3a makes it possible to execute an operation for capturing the fundus image Ef' and an operation for capturing a tomographic image, in the same manner as when operating a traditional fundus camera.

As shown in FIG. 6, the operation panel 3a is provided with, for example, a menu switch 301, a split switch 302, an imaging light amount switch 303, an observation light amount switch 304, a jaw holder switch 305, a photographing switch 306, a zoom switch 307, an image switching switch 308, a fixation target switching switch 309, a fixation target position adjusting switch 310, a fixation target size switching switch 311 and a mode switching knob 312.

The menu switch 301 is a switch operated to display a certain menu display for a user to select and specify various types of menus (such as a photographing menu for photographing a 2-dimensional image of the surface of the fundus oculi Ef and a tomographic image, and a setting menu for inputting various types of settings).

When this menu switch 301 is operated, the operation signal is input to the controller 210. The controller 210 causes the touch panel monitor 11 or the display 240A to display a menu screen in response to the input of the operation signal. A controller (not shown) may be provided in the fundus camera unit 1A so as to cause the touch panel monitor 11 to display the menu screen.

The split switch 302 is a switch operated to switch the light on and off of the split bright line for focusing (e.g., see JP Patent laid-open No. H9-66031 or the like. Also referred to as split target, split mark and so on.). The configuration for projecting this split bright line onto the eye E (split bright line projection part) is housed, for example, in the fundus camera unit 1A (omitted in FIG. 1).

When the split switch 302 is operated, the operation signal is input to the controller 210 (or the above controller in the fundus camera unit 1A; the same hereinafter). The controller 210 projects the split bright line onto the eye E by controlling the split bright line projection part in response to the input of this operation signal.

The imaging light amount switch 303 is a switch operated to adjust the emitted light amount of the imaging light source 103 (photographing light amount) depending on the state of the eye E (such as the degree of opacity of the lens). This imaging light amount switch 303 is provided with, for example, a photographing light amount increasing switch "+" for increasing the photographing light amount, a photographing light amount decreasing switch "−" for decreasing the photographing light amount, and a reset switch (button in the middle) for setting the photographing light amount to a certain initial value (default value).

When one of the imaging light amount switches 303 is operated, the operation signal is input to the controller 210. The controller 210 adjust the photographing light amount by controlling the imaging light source 103 in response to the operation signal having been input.

The observation light amount switch 304 is a switch operated to adjust the emitted light amount (observation light amount) of the observation light source 101. The observation light amount switch 304 is provided with, for example, an observation light amount increasing switch "+" for increasing the observation light amount, and an observation light amount decreasing switch "−" for decreasing the observation light amount.

When one of the observation light amount switches 304 is operated, the operation signal is input to the controller 210. The controller 210 adjusts the observation light amount by controlling the observation light source 101 in response to the operation signal that was input.

The jaw holder switch 305 is a switch to move the position of the jaw holder 6 shown in FIG. 11. This jaw holder switch 305 is provided with, for example, an upward movement switch (upward triangle) for moving the jaw holder 6 upward and a downward movement switch (downward triangle) for moving the jaw holder 6 downward.

When one of the jaw holder switches 305 is operated, the operation signal is input to the controller 210. The controller 210 moves the jaw holder 6 upward or downward by controlling a jaw holder movement mechanism (not shown) in response to the operation signal having been input.

The photographing switch 306 is a switch used as a trigger switch for capturing a 2-dimensional image of the surface of the fundus oculi Ef or a tomographic image of the fundus oculi Ef.

When the photographing switch 306 is operated in a state where a menu to photograph a 2-dimensional image is selected, the controller 210 that has received the operation signal controls the imaging light source 103 to emit photographing illumination light, and also causes the display 240A or the touch panel monitor 11 to display a 2-dimensional image of the surface of the fundus oculi Ef, based on the video signal output from the imaging device 10 that has detected the fundus reflection light.

On the other hand, when the photographing switch 306 is operated in a state where a menu to capture a tomographic image is selected, the controller 210 that has received the operation signal controls the low coherence light source 160 to emit the low coherence light L0, controls the Galvano mirrors 141A and 141B to scan the signal light LS, and also causes the display 240A or the touch panel monitor 11 to display a tomographic image of the fundus oculi Ef formed by the image forming part 220 (and image processor 230), based on the detection signal output from the CCD 184 that has detected the interference light LC.

The zoom switch 307 is a switch operated to change the angle of view (zoom magnification) for photographing of the fundus oculi Ef. Every time this zoom switch 307 is operated, for example, 45 degree and 22.5 degree of photographing angles of view is set alternately.

When this zoom switch 307 is operated, the controller 210 that has received the operation signal controls a variable magnifying lens driving mechanism (not shown) to move the variable magnifying lens 124 along the optical axial direction, thereby changing the photographing angle of view.

The image switching switch 308 is a switch operated to switch displaying images. When the image switching switch 308 is operated in a state where a fundus oculi observation image (a 2-dimensional image of the surface of the fundus oculi Ef based on the video signal from the imaging device 12) is displayed on the display 240A or the touch panel monitor 11, the controller 210 that has received the operation signal controls the display 240A or the touch panel monitor 11 to display the tomographic image of the fundus oculi Ef.

On the other hand, when the image switching switch 308 is operated in a state where a tomographic image of the fundus oculi is displayed on the display 240A or the touch panel monitor 11, the controller 210 that has received the operation signal controls the display 240A or the touch panel monitor 11 to display the fundus oculi observation image.

The fixation target switching switch 309 is a switch operated to switch the position of the internal fixation target displayed by the LCD 140 (i.e. the projection position of the internal fixation target on the fundus oculi Ef). By operating this fixation target switching switch 309, the display position of the internal fixation target can be switched, for example, among "fixation position to capture the image of the peripheral region of the center of the fundus oculi," "fixation position to capture the image of the peripheral region of macula lutea" and "fixation position to capture the image of the peripheral region of papilla," in a circulative fashion.

The controller 210 controls the LCD 140, in response to the operation signal from the fixation target switching switch 309, to display the internal fixation target in the different positions on its display surface. The display positions of the internal fixation target corresponding to the above three fixation positions, for example, are preset based on clinical data or are set for each eye E (image of the fundus oculi Ef) in advance.

The fixation target position adjusting switch 310 is a switch operated to adjust the display position of the internal fixation target. This fixation target position adjusting switch 310 is provided with, for example, an upward movement switch for moving the display position of the internal fixation target upward, a downward movement switch for moving it downward, a leftward movement switch for moving it leftward, a rightward movement switch for moving it rightward, and a reset switch for moving it to a certain initial position (default position).

Upon reception of the operation signal from either of these switches of the fixation target position adjusting switch 310, the controller 210 controls the LCD 140 to move the display position of the internal fixation target, in response to the operation signal.

The fixation target size switching switch 311 is a switch operated to change the size of the internal fixation target. When this fixation target size switching switch 311 is operated, the controller 210 that has received the operation signal controls the LCD 140 to change the display size of the internal fixation target. The display size of the internal fixation target can be changed, for example, between "normal size" and "enlarged size," alternately. As a result, the size of the projection image of the fixation target projected onto the fundus oculi Ef is changed. Upon reception of the operation signal from the fixation target position adjusting switch 311, the controller 210 controls the LCD 140 to change the display size the internal fixation target, in response to the operation signal.

The mode switching knob 312 is a knob rotationally operated to select various types of photographing modes (such as a fundus oculi photographing mode to photograph a 2-dimensional image of the fundus oculi Ef, a B-scan mode to perform B-scan of the signal light LS, and a 3-dimensional scan mode to have the signal light LS to be scanned 3-dimensionally). In addition, this mode switching knob 312 may be capable of selecting a replay mode to replay a captured 2-dimensional image or a tomographic image of the fundus oculi Ef. In addition, it may be capable of selecting a photographing mode to control so that the photographing of the fundus oculi Ef would be performed immediately after scanning of the signal light LS. Control of each part of the device for causing the fundus observation device 1 to execute operations corresponding to the respective modes is executed by the controller 210.

The feature of control of scanning of the signal light LS by the controller 210, and the feature of processing to the detection signal from the OCT unit 150 by the image forming part 220 and the image processor 230 will be respectively described below. Furthermore, an explanation regarding the process of the image forming part 220, etc., to the video signal from the fundus camera unit 1A will be omitted because it is the same as the conventional process.

Regarding the Signal Light Scanning

Scanning of the signal light LS is performed by changing the facing direction (position) of the reflecting surfaces of the galvanometer-mirrors 141A and 141B of the scanning unit 141 in the fundus camera unit 1A. By controlling the mirror drive mechanisms 241 and 242 respectively, the controller 210 changes the facing directions of the reflecting surfaces of the galvanometer-mirror 141A and 141B respectively, and scans the signal light LS on the fundus oculi Ef.

Once the facing direction of the reflecting surface of the galvanometer-mirror 141A is changed, the signal light LS is scanned in a horizontal direction (x-direction in FIG. 1) on the fundus oculi Ef. Whereas, once the facing direction of the reflecting surface of the galvanometer-mirror 141B is changed; the signal light LS is scanned in a vertical direction (y-direction in FIG. 1) on the fundus oculi Ef. Furthermore, by changing the facing directions of the reflecting surfaces of both the galvanometer-mirrors 141A and 141B simultaneously, the signal light LS may be scanned in the composed direction of the x-direction and y-direction. That is, by controlling these two galvanometer-mirrors 141A and 141B, it is possible to scan the signal light LS in any direction on the x-y plane.

Figure 8A:
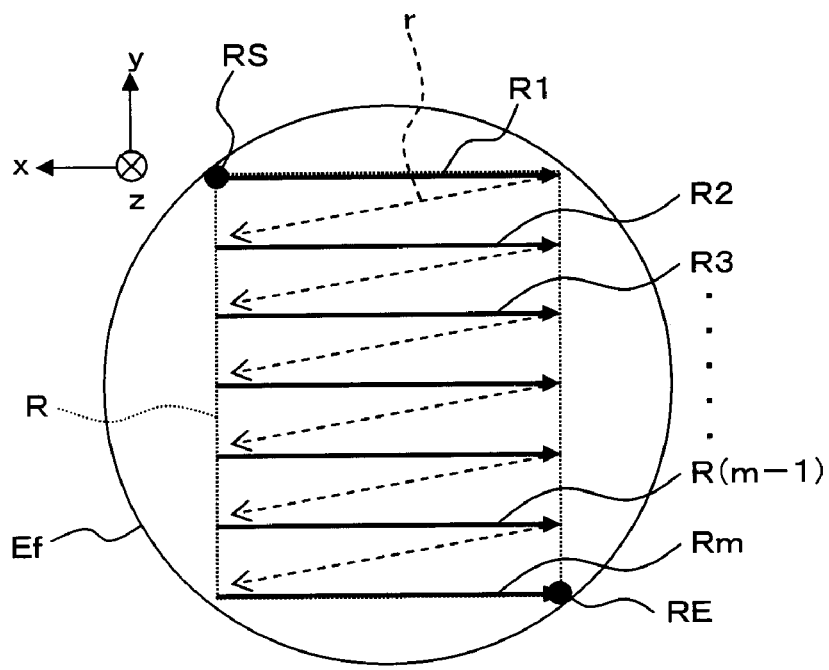
FIG. 8A shows one example of the feature of scan of signal light when a fundus oculi is seen from the incident side of the signal light with respect to an eye.
Figure 8B:
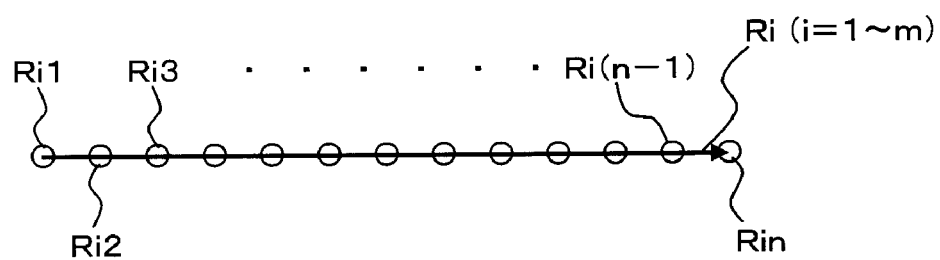
FIG. 8B shows one example of the feature of arrangement of scanning points on each scanning line.

FIG. 8 shows one example of the feature of scanning of the signal light LS for forming images of the fundus oculi Ef. FIG. 8A shows one example of the feature of scanning of the signal light LS, when the fundus oculi Ef is seen from a direction that the signal light LS enters the eye E (that is, seen in +direction of z from −direction of z in FIG. 1). Furthermore, FIG. 8B shows one example of the feature of arrangement of scanning points (positions at which image measurement is carried out; target position of the signal light LS) on each scanning line on the fundus oculi Ef.

As shown in FIG. 8A, the signal light LS is scanned within a rectangular-shaped scanning region R that has been preset. Within this scanning region R, plural (m number of) scanning lines R1 through Rm are set in the x-direction. When the signal light LS is scanned along the respective scanning lines Ri (i=1 through m), detection signals of the interference light LC are generated.

Herein, a direction of each scanning line Ri will be referred to as the "main scanning direction" and a direction orthogonal thereto will be referred to as the "sub-scanning direction". Accordingly, the scanning of the signal light LS in the main scanning direction is performed by changing the facing direction of the reflecting surface of the galvanometer-mirror 141A, and the scanning in the sub-scanning direction is performed by changing the facing direction of the reflecting surface of the galvanometer-mirror 141B.

On each scanning line Ri, as shown in FIG. 8B, plural (n number of) scanning points Ri1 through Rin are preset.

In order to execute the scanning shown in FIG. 8, the controller 210 firstly controls the galvanometer-mirrors 141A and 141B to set the target of the signal light LS entering into the fundus oculi Ef at a scan start position RS (scanning point R11) on the first scanning line R1. Subsequently, the controller 210 controls the low coherence light source 160 to flush the low coherence light L0, thereby emitting the signal light LS to the scan start position RS. The CCD 184 receives the interference light LC based on the fundus reflection light of this signal light LS at the scan start position RS, and outputs the detection signal to the controller 210.

Next, the controller 210 controls the galvanometer-mirror 141A to scan the signal light LS in the main scanning direction and set the incident target at a scanning point R12, and makes the low coherence light L0 flushed to make the signal light LS enter into the scanning point R12. The CCD 184 receives the interference light LC based on the fundus reflection light of this signal light LS at the scanning point R12, and then outputs the detection signal to the controller 210.

Likewise, the controller 210 obtains detection signals output from the CCD 184 in response to the interference light LC for each scanning point, by flushing the low coherence light L0 at each scanning point while shifting the incident target of the signal light LS from scanning point R13 to R14, - - -, R1 (n−1), and R1n in order.

Once the measurement at the last scanning point R1n of the first scanning line R1 is finished, the controller 210 controls the Galvano mirrors 141A and 141B simultaneously to shift the incident target of the signal light LS to the first scanning point R21 of the second scanning line R2 following a line switching scan r. Then, by conducting the previously described measurement on each scanning point R2j (j=1 through n) of this second scanning line R2, a detection signal corresponding to each scanning point R2j is obtained.

Likewise, the measurement is conducted for each of the third scanning line R3, - - -, the m−1th scanning line R(m−1), the mth scanning line Rm to obtain the detection signal corresponding to each scanning point. Symbol RE on a scanning line Rm is a scan end position corresponding to a scanning point Rmn.

As a result, the controller 210 obtains m×n number of detection signals corresponding to m×n number of scanning points Rij (i=1 through m, j=1 through n) within the scanning region R. Hereinafter, a detection signal corresponding to the scanning point Rij may be represented by Dij.

Such interlocking control of the shifting of scanning points and the emission of the low coherence light L0 may be realized by synchronizing, for instance, timing for transmission of control signals to the mirror drive mechanisms 241 and 242 and timing for transmission of control signals (output request signals) to the low coherence light source 160.

As described above, when each of the galvanometer-mirrors 141A and 141B is operated, the controller 210 stores the position of each scanning line Ri and the position of each scanning point Rij (coordinates on the x-y coordinate system) as information representing the content of the operation. This stored content (scanning point coordinate information) is used in an image forming process as in conventional one.

Regarding Image Processing

Next, one example of a process on OCT images (tomography images of the fundus oculi Ef) by the image forming part 220 and the image processor 230 will be described.

The image forming part 220 executes the formation process of tomographic images of the fundus oculi Ef along each scanning line Ri (main scanning direction). The image processor 230 executes the formation process of a 3-dimensional image of the fundus oculi Ef based on these tomographic images formed by the image forming part 220.

The formation process of a tomographic image by the image forming part 220, as in the conventionally one, includes a 2-step arithmetic process. In the first step of the arithmetic process, based on a detection signal Dij corresponding to each scanning point Rij, an image in the depth-wise direction (z-direction in FIG. 1) of the fundus oculi Ef at the scanning point Rij is formed.

Figure 9:
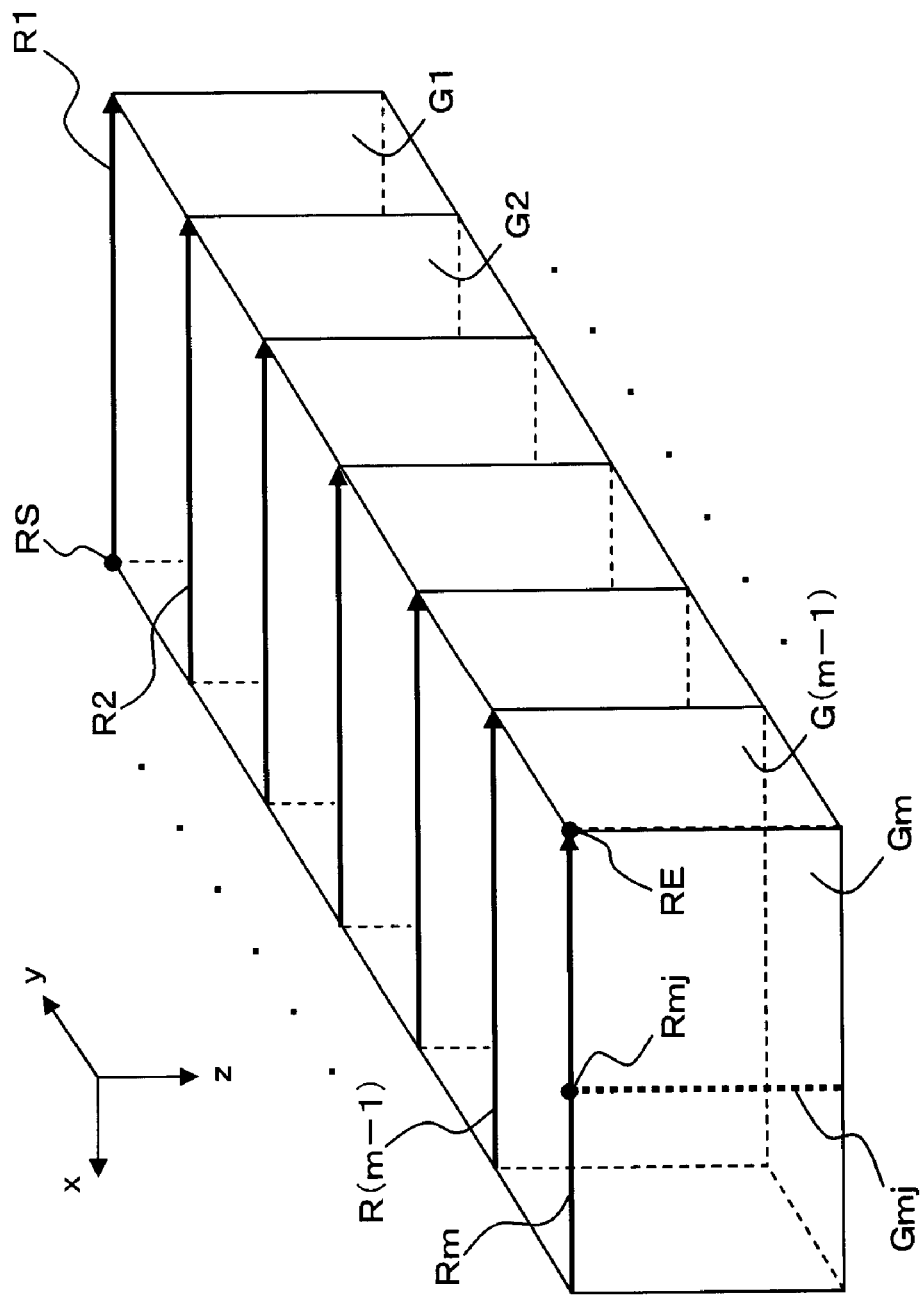
FIG. 9 is a schematic diagram showing one example of the feature of scan of signal light and the feature of a tomographic image formed along each scanning line in the preferred embodiment of the fundus observation device according to the present invention.

FIG. 9 shows a feature of (a group of) tomographic images formed by the image forming part 220. In the second step of the arithmetic process, on each scanning line Ri, based on the images in the depth-wise direction at the n number of scanning points Ri1 through Rin, a tomographic image Gi of the fundus oculi Ef along the scanning line Ri is formed. Then, the image forming part 220 determines the arrangement and the distance of the scanning points Ri1 through Rin referring to the positional information (scanning point coordinate information described before) of the scanning points Ri1 through Rin, and forms a tomographic image Gi along this scanning line Ri.

Through the above process, m number of tomographic images (a group of tomographic images) G1 through Gm at different positions in the sub-scanning direction (y-direction) are obtained. Image data of each of these tomographic images G1 through Gm corresponds to the image data Ga of tomographic image in FIG. 7 (described later).

Next, the formation process of a 3-dimensional image of the fundus oculi Ef by the image processor 230 will be explained. A 3-dimensional image of the fundus oculi Ef is formed based on the m number of tomographic images obtained through the above arithmetic process. The image processor 230 forms a 3-dimensional image of the fundus oculi Ef by performing a known interpolating process to interpolate an image between the adjacent tomographic images Gi and G (i+1).

Then, the image processor 230 determines the arrangement and the distance of each scanning line Ri while referring to the positional information of each scanning line Ri to form this 3-dimensional image. For this 3-dimensional image, a 3-dimensional coordinate system (x, y, z) is set, based on the positional information (the scanning point coordinate information) of each scanning point Rij and the z-coordinate in the depth-wise image.

Furthermore, based on this 3-dimensional image, the image processor 230 can form a tomographic image of the fundus oculi Ef at a cross-section in any direction other than the main scanning direction (x-direction). Once the cross-section is designated, the image processor 230 determines the position of each scanning point (and/or an interpolated depth-wise image) on this designated cross-section, and extracts a depth-wise image at each determined position (and/or an interpolated depth-wise image), thereby forming a tomographic image of the fundus oculi Ef at the designated cross-section by arranging plural extracted depth-wise images.

Furthermore, an image Gmj shown in FIG. 9 represents an image in the depth-wise direction (z-direction) at the scanning point Rmj on the scanning line Rm. A depth-wise image at each scanning point Rij on the scanning line Ri formed by the first-step arithmetic process is represented as "image Gij."

Detailed Configuration of the Arithmetic and Control Unit

A detailed configuration of the arithmetic and control unit 200 will be described referring to FIG. 7. Herein, the controller 210 and the image processor 230 of the arithmetic and control unit 200 will be detailed specifically.

The controller 210 is provided with a main controller 211, an image storage 212, an information storage 213, and a control information-generating part 214. In addition, the image processor 230 is provided with a dispersion-correcting part 231. Each part constituting the controller 210 and the image processor 230 will be described hereinafter.

Dispersion-Correcting Part

First, the dispersion-correcting part 231 of the image processor 230 will be described. While passing through the inside (crystal lens or corpus vitreum) of the eye E, the signal light LS is affected by the dispersion of tissues of the inside of the eye E. This effect of dispersion is also reflected in the interference light LC. The dispersion-correcting part 231 corrects the effect of dispersion of the eye E on the fundus image Ef or the tomographic image Ga. A heretofore known dispersion correction algorithm may optionally be applied to this dispersion correction process.

As well as in a general dispersion correction process, the dispersion-correcting part 231 applies the above dispersion correction algorithm using a predetermined correction parameter to image data of the fundus image Ef or the tomographic image Ga (image to be corrected), thereby correcting the effect of dispersion on the image to be corrected. This dispersion-correcting part 231 functions as one example of the "dispersion-correcting part" of the present invention.

Main Controller

Next, the configuration of the controller 210 will be described. First, the main controller 211 controls each part of the fundus observation device 1 described above, and comprises the microprocessor 201 performing a process according to the control program 204a.

In addition, the main controller 211 generates date and time information representing the date and time of examination of the fundus oculi Ef (capture of the fundus image Ef' and the tomographic image Ga). This date and time information should include at least the date of the examination (the time of the examination does not need to be included). This main controller 211 functions as one example of the "controller" of the present invention.

Image Storage

The image storage 212 stores image data 212a of a 2-dimensional image of the surface of the fundus oculi Ef (fundus oculi image) and image data Ga of a tomographic image formed by the image forming part 220. A process of storing image data into the image storage 212 and a process of reading out image data from the image storage 212 are executed by the main controller 211. The image storage 212 includes a storage device such as the hard disk drive 204.

Information Storage

The information storage 213 stores control information 213a on the content of control of each part of the device by the main controller 211 when the fundus image Ef' or the tomographic image Ga is formed. The control information 213a is stored on the information storage 213, together with (or, in association with) examination information on examination in which the image has been captured, such as patient information like patient identification information of a patient whose fundus image Ef,' a tomographic image Ga, or the like has been photographed, and the date and time information when imaging has been performed.

The control information 213a will be described in further detail. This control information 213a includes information, such as scan control information on scan of the signal light LS, projection position control information on the position of projection of the internal fixation target onto the fundus oculi Ef, reference light amount control information on the reduction of the amount of the reference light LR by the density filter 173, and dispersion correction parameters in the dispersion correction process of the fundus image Ef' or the tomographic image Ga. Hereinafter, such information included in the control information 213a will each be described.

Scan Control Information

First, the scan control information will be described. This scan control information is information representing the scanning feature of the target position of the signal light LS onto the fundus oculi Ef by the scanning unit 141 (galvanometer-mirrors 141A and 141B, mirror drive mechanisms 241 and 242) at the time of formation of the tomographic image Ga of the fundus oculi Ef. Herein, the "scanning feature" includes at least the features regarding arrangement, interval, track, and so on of the target position of the signal light LS to the fundus oculi Ef.

A case where the signal light LS is scanned as shown in FIG. 8 will be described as an example. In the scanning example shown in FIG. 8, the signal light LS is first emitted toward the scan start position RS (scanning point R11). Next, the target position is moved to the scanning point R12 distant from the scan start position RS by a predetermined distance (=constant=$\Delta x$) in the −x-direction, and then the signal light LS is emitted. Similarly, the signal light LS is emitted to each scanning point R1$j$ while the target position of the signal light LS is subsequently moved by $\Delta x$ in the −x-direction, and then scanning along the scanning line R1 is terminated.

When the signal light LS is emitted to the last scanning point R1$n$ on the scanning line R1, the target position is moved to the first scanning point R21 on the second scanning line R2, and then, the signal light LS is emitted. Herein, an interval (in the y-direction) of the adjacent scanning lines Ri and R (i+1) will be denoted by $\Delta y$. Next, scanning at each scanning point R2$j$ on the scanning line R2 is performed, as in the case of the scan on the first scanning line R1. In this manner, the signal light LS is emitted while the target position is subsequently moved to the last scanning point Rmn on the last (mth) scanning line Rm.

The scan control information according to this scanning example is, for example, as follows. As described above, scan of the signal light LS in the x-direction is performed by controlling the galvanometer-mirror 141A, and scan in the y-direction is performed by controlling the galvanometer-mirror 141B.

The scan control information at this time includes, for example, the following five items of information:

(i) scan start position information: information representing the positions of the galvanometer-mirrors 141A and 141B when the signal light LS is emitted to the scan start position RS (scanning point R11);

(ii) x-direction scanning interval information: information on displacement $\Delta\theta x$ of the position of the galvanometer-mirror 141A (facing direction of the reflection surface), corresponding to the interval $\Delta x$ between the adjacent scanning points Rij and Ri (j+1) in the direction of the scanning line Ri (x-direction);

(iii) y-direction scanning interval information: displacement $\Delta\theta y$ of the position of the galvanometer-mirror 141B (facing direction of the reflection surface), corresponding to the interval $\Delta y$ between the adjacent scanning lines Ri and R (i+1);

(iv) information on the number of scanning lines representing the number of the scanning lines R1 through Rm (m number of scanning lines); and (v) information on the number of scanning points representing the number of the scanning points Ri1 through Rin on each scanning line Ri.

These pieces of information (i) through (v) are information that represent the position of each scanning point Rij in scan of the signal light LS shown in FIG. 8, namely, information that represents the positions of the galvanometer-mirrors 141A and 141B for scanning so as to emit the signal light LS to each scanning point Rij (the information on the arrangement and the interval of the target positions described above). These pieces of information (i) through (v) are information that represents the scanning position of the signal light LS, such as the position and number of the scanning point Rij and furthermore the interval between adjacent scanning points, and correspond to one example of the "scanning position information" according to the present invention.

Herein, the scan control information may include only information representing a form of arrangement of scanning points (arrangement information), or may include only an interval between adjacent scanning points (interval in the x-direction and/or interval in the y-direction).

Furthermore, the scan control information may include information representing the track of target positions of the signal light LS (scanning track information). This scanning track information is information that represents the order of emission of the signal light LS when the target position of the signal light LS is subsequently moved to a plurality of scanning points.

For example, in scan of the scanning points R11 through Rmn arranged in m rows and n columns as shown in FIG. 8, first, the target positions are sequentially scanned in the −x-direction from scanning point R11 to the scanning point R1$n$ on the first row (scanning line R1). Secondly, the signal light LS is moved to the first scanning point R21 on the second row (scanning line R2) (line switching scan r), and then the target positions are sequentially scanned in the −x-direction from the scanning point R21 to the scanning point R2n on this second row. Such scanning is performed up to the last scanning point Rmn on the last row (scanning line Rm).

In this case, as the scanning track information of the scanning points R11 through Rmn arranged in m rows and n columns, an emission order "R11→R12→ . . . →R1n→R21→R22→ . . . →Rmn" can be obtained. Assuming that the arrangement information (m rows and n columns) of the scanning points is included in the scan control information, this scanning track information becomes information representing a zigzag scanning track of the signal light LS that sequentially moves on the parallel scanning lines R1 through Rm in the −x-direction as shown in FIG. 8A.

It is clear that two or more different scanning tracks can be defined, even if arrangement of the scanning points is the same. For example, even in the arrangement of m rows and n column shown in FIG. 8, it is possible to apply a scanning track such as scanning odd-number rows in the −x-direction and scanning even-number rows in the +x-direction, or it is possible to apply a scanning track such as scanning along n number of scanning lines along the y-direction.

In addition, as disclosed in Patent Application No. 2005-337628 by the inventors of the present invention, in the case of scanning (scan for the position correction of tomographic image; skewed scan) also in a direction crossing each of a plurality of scanning lines (direction crossing the main scanning direction), it is possible to include information representing the track of this skewed scan in the scanning track information.

In addition, in the case of performing the B-scan described above, in the case of scanning a plurality of scanning points along a helical track, or in the case of scanning along a concentric track, it is possible to include information representing the track in the scanning track information. It is needless to say that it is possible, even when scanning along another pattern of track, to include information representing the track in the scanning track information.

In addition, also in a case where the arrangement information and/or interval information of a plurality of scanning points are not included, it is possible to form the scanning track information. For example, it is possible to form scanning track information representing a scanning pattern (type) such as a zigzag pattern, a skewed scan, a helical pattern, and a concentric pattern.

Projection Position Control Information

The projection position control information is information that represents the position of projection of the internal fixation target onto the fundus oculi Ef. The internal fixation target is to guide and project the image displayed on the LCD 140 onto the fundus oculi Ef as described above. The projection position control information includes, for example, information representing the display position of (the image of) the internal fixation target on the LCD 140 when the fundus image Ef' or the tomographic image Ga is captured.

Generally, pixels are arranged two-dimensionally on the display screen of a display device such as an LCD, and coordinate values of a two-dimensional coordinate system are pre-assigned to each pixel. When the internal fixation target is displayed on the LCD 140, the main controller 211 makes an image displayed at a predetermined position on the display screen by designating pixels forming the image of the internal fixation target. At this time, the main controller 211 determines the display position of the image of the internal fixation target, in response to operations on the fixation target-switching switch 309 and the fixation target position-adjusting switch 310 of the operation panel 3a described above.

Reference Light Amount Control Information

The reference light amount control information is information that represents the amount of the reference light LR reduced by the density filter 173 when the tomographic image Ga is captured. The density filter 173 is rotated by the density filter drive mechanism 244 as described above, thereby changing the reduction amount of the reference light LR.

At this time, the main controller 211 controls the density filter drive mechanism 244 to rotate the density filter 173, for example, in response to an operation on the operation part 240B. Consequently, the density filter 173 is placed on the optical path of the reference light LR in the state where of reducing the amount of the reference light LR by the reduction amount designated by that operation.

The reference light amount control information includes information representing the placement state of the density filter 173 at this time. This information can be represented, for example, as a rotation angle from a reference position (previously set) in the rotation of the density filter 173.

Dispersion Correction Parameter

The dispersion correction parameter is a parameter used in the dispersion correction process of the fundus image Ef' or the tomographic image Ga by the dispersion-correcting part 231 described above.

Control Information-Generating Part

The control information-generating part 214 generates the control information 213a based on the content of control of each part of the device by the main controller 211 when the fundus image Ef' or the tomographic Ga is captured. More specifically, the control information-generating part 214 generates the control information 214a, for example, based on the content of control of each part of the device, depending on the setting set by a user with the operation panel 3a, the operation part 240B, or the like.

One example of a process of generating the scan control information will be described. The scan control information is information that represents the scanning feature of the target position of the signal light LS when the tomographic image Ga is captured, as described above. The control information-generating part 214 obtains the content of control of the mirror drive mechanisms 241 and 242 by the main controller 211 (namely, the feature of change of the facing directions of the reflection surfaces of the galvanometer-mirrors 141A and 141B by the mirror drive mechanisms 241 and 242), thereby generating the scan control information.

For example, when the signal light LS is scanned as shown in FIG. 8, the main controller 211 controls the mirror drive mechanisms 241 and 242, whereby the signal light LS is sequentially emitted to the scanning points Rij in m rows and n columns. The main controller 211 sends, to the control information-generating part 214, the content of the control signal transmitted to the mirror drive mechanisms 241 and 242 (scan control information; the rotation angles of the galvanometer-mirrors 141A and 141B, represented by number of control pulses sent to the mirror drive mechanisms 241 and 242, for example).

The control information-generating part 214 correspondingly generates the scan start position information, the x-direction scanning interval information, the y-direction scanning interval information, the information of the number of scanning lines, the information of the number of scanning points, and the scanning track information described above, based on this scan control information, and defines them as the scan control information of the scan control information 213a.

Next, one example of a process of generating the projection position control information will be described. The projection position control information is information that represents the projection position of the internal fixation target onto the fundus oculi Ef, as described above. For example, when an image of the internal fixation target is displayed on the LCD 140, the main controller 211 sends information of the coordinate values of pixels of that image (projection control information; coordinate values in the two-dimensional coordinate system described above) to the control information-generating part 214.

The control information-generating part 214 defines the coordinate values of the pixels of the internal fixation target indicated in this projection control information, namely, information on the display position of the image of the internal fixation target on the display screen of the LCD 140, as the projection position control information of the control information 213a.

Next, a process of generating the reference light amount control information will be described. The reference light amount control information is information that represents the amount of the reference light LR reduced by the density filter 173, as described above. The control information-generating part 214 receives, from the main controller 211, the content of control of the density filter drive mechanism 244, or in other words, information of the rotation angle of the density filter 173 by the density filter drive mechanism 244 (light amount control information), for definition similar to the reference light amount control information of the control information 213a.

Herein, the light amount control information is information that includes the rotation angle from the reference position described above (e.g., represented by the number of control pulses sent to the density filter drive mechanism 244).

Next, a process of generating the dispersion correction parameter will be described. Upon correction dispersion of the tomographic image Ga, the dispersion-correcting part 231 sends the dispersion correction parameter employed in this process to the main controller 211. The main controller 211 sends this dispersion correction parameter to the control information-generating part 214. The control information-generating part 214 generates the control information 213a, including this dispersion correction parameter.

When a plurality of dispersion correction parameters stored in advance are alternately used, for example, it may also be configured to provide identification information to each correction parameter in advance and to generate the control information 213a, including this identification information.

The main controller 211 stores the control information 213a generated by the control information-generating part 214 on the information storage 213. At this time, the main controller 211 stores, on the information storage 213, the date and time information representing the obtaining date and time of the fundus image Ef or the tomographic image Ga and patient identification information input by the reading device or the user interface 240 described above, each associated with the control information 213a. The date and time information representing the date and time of the examination and the patient identification information regarding the patient subject to the examination may be collectively referred to as examination information.

Operation

Figure 10:
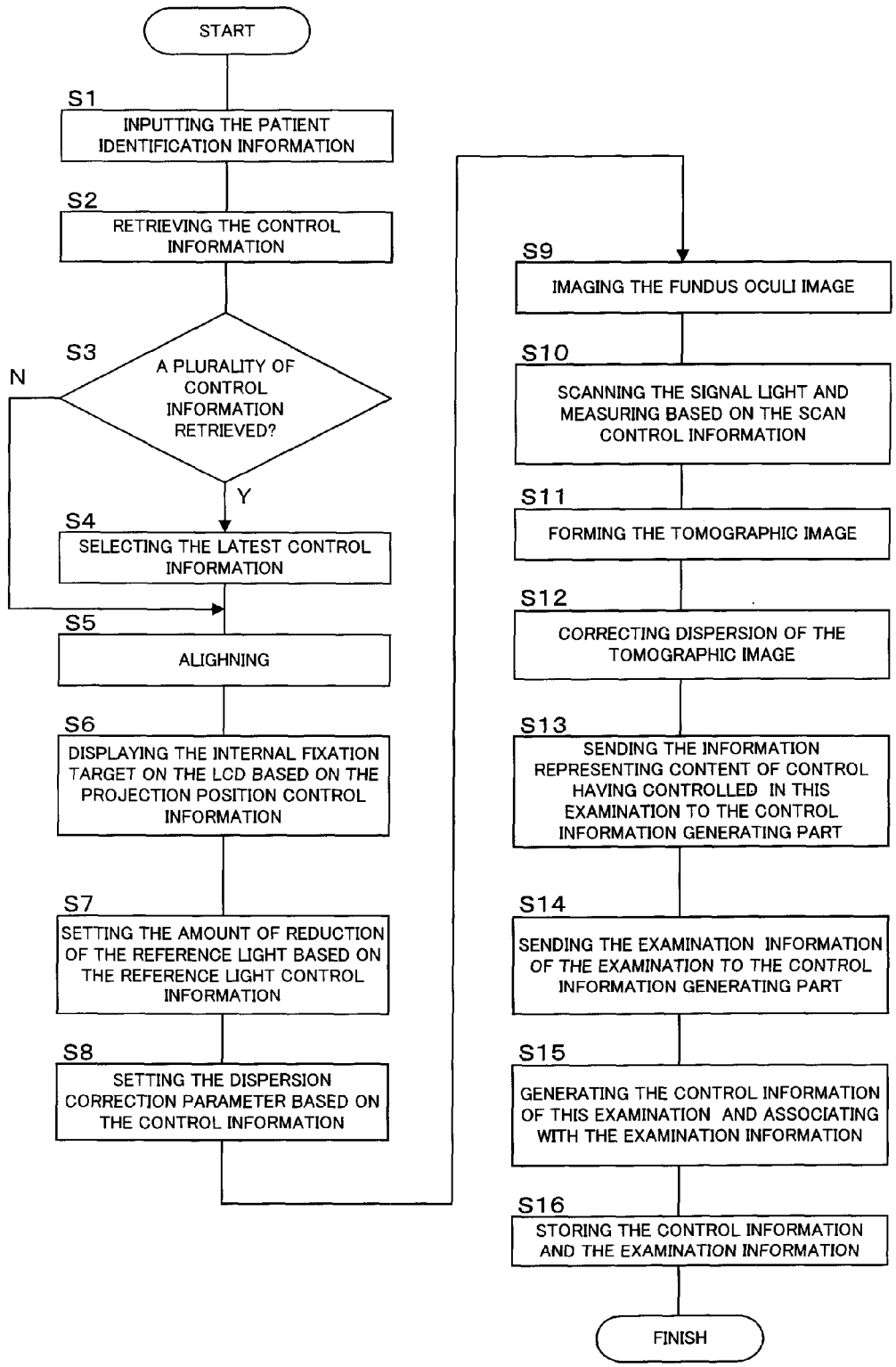
FIG. 10 is a flowchart showing one example of the usage mode of the preferred embodiment of the fundus observation device according to the present invention.

An operation of the fundus observation device 1 having the above constitution will be described. FIG. 10 is a flowchart showing one example of usage patterns of the fundus observation device 1.

It is assumed as a premise that the information storage 213 stores the control information 213a corresponding to an examination that has been practiced in the past (capturing of the fundus image Ef or the tomographic image Ga). The control information 213a is stored associated with the corresponding examination information, and is stored for each patient as well as each examination, based on the patient identification information and the date and time information.

Hereinafter, a case in which an examination (capturing of an image) is performed on a patient to be reexamined in the course observation or the like will be described. In the case of examination on a new patient, setting of each part of the fundus observation device 1 will be performed by a manual operation or the like, as in the conventional one.

First, the patient identification information is input, using a reading device such as a card reader or the user interface 240 (S1). The main controller 211 retrieves the control information 213a associated with the input patient identification information from the information storage 213 (S2). When there are a plurality of the retrieved control information 213a (S3; Y), the main controller 211 selects the latest control information 213a by referencing the date and time information associated with each control information 213a (S4). This latest control information 213a is the control information from the last consultation.

A user (examiner) positions the jaw of a patient (subject to be examined) on the jaw holder 6 and aligns the fundus camera unit 1A with the eye E (S5).

The main controller 211 causes the LCD 140 to display (the image of) the internal fixation target on the LCD 140, based on the projection position control information included in the control information 213a (S6). Consequently, the internal fixation target is displayed at the same display position of the LCD 140 as at the last consultation, and the internal fixation target is projected onto almost the same position on the fundus oculi Ef as in the last consultation. Herein, in the alignment of step S5, a minute error may intervene compared to the last consultation, so the internal fixation target will be projected onto "almost" the same position as in the last consultation.

Herein, an observation image of the fundus oculi Ef is displayed on the touch panel monitor 11 or the display 240A, for example, by turning on the observation light source 101. Then, while this observation image is observed, the fixation position of the eye E is adjusted by operating the fixation target position-adjusting switch 310, if necessary.

Next, the main controller 211 controls the density filter drive mechanism 244 to rotate the density filter 173, based on the reference light reduction information included in the control information 213a (S7). Consequently, the same amount of reduction of the reference light LR as in the last consultation is set.

In addition, the main controller 211 sends the dispersion correction parameter included in the control information 213a to the dispersion-correcting part 231 (S8).

In addition, various settings required for performing image photography of the fundus oculi Ef are made accordingly.

When the setting of each part of the device is finished, the user photographs the fundus image Ef of the eye E by operating the photographing switch 306 (S9). The image data 212a of the photographed fundus image Ef is saved in the image storage 212 by the main controller 211.

Then, the main controller 211 controls the mirror drive mechanisms 241 and 242 according to the scan control information included in the control information 213a to scan the target position of the signal light LS (irradiation target position), and at the same time, turns on the low-coherence light source 160 at the timing when the target position is scanned on each scanning point (Rij) (that is, takes measurement for capturing the tomographic image) (S10).

The signal light LS emitted to each scanning point is overlapped with the reference light LR, whereby the interference light LC is generated. The generated interference light LC is detected by means of the CCD 184 of the spectrometer 180.

The image-forming part 220 forms image data Ga of the tomographic image of the fundus oculi Ef based on the detection signal from the CCD 184 that has detected the interference light LC (S11).

The main controller 211 sends the formed image data Ga of the tomographic image to the dispersion-correcting part 231 of the image processor 230. The dispersion-correcting part 231 corrects the dispersion of the image data Ga of the tomographic image by employing the dispersion correction parameter received in step S8 (S12). The dispersion-corrected image data Ga is sent to the main controller 211 and is then saved in the image storage 212.

The main controller 211 sends, to the control information-generating part 214, information that represents content of control when having controlled each part of the device in the examination (image capturing) this time (S13). Information that represents the content of control includes, for example, information representing the display position of the internal fixation target in step S6 (if adjusted, the adjusted display position), information representing the amount of reduction of the reference light LR set in step S7, information representing the scanning feature of the signal light LS in step S10, the dispersion correction parameter applied in the dispersion correction process of step S12, and so forth.

In addition, the main controller 211 sends the date and time information of this examination along with the patient identification information (examination information) input in step S1 to the control information-generating part 214 (S14).

The control information-generating part 214 generates the control information 213*a* of the examination this time based on the information received in step S13, and at the same time, associates this control information 213*a* with the information received in step S14 (examination information) (S15). The main controller 211 causes the information storage 213 to store the control information 213*a* and the examination information of the examination this time (S16).

This is the end of the examination this time. In the next examination, the control information 213*a* of the examination this time stored in step S16 will be referenced.

Action and Effect

The action and effect of the aforementioned fundus observation device 1 will be described. This fundus observation device 1 forms the fundus image Ef' and the tomographic image Ga of the fundus oculi Ef, stores the control information 213*a* indicating the content of control of each part of the device when the fundus image Ef' or the tomographic image Ga has been formed, and acts so as to control each part of the device based on the stored control information 213*a* when a new image is formed.

Herein, information included in the control information 213*a* includes the scan control information regarding the scan of the signal light LS, the projection position control information regarding the projection position of the internal fixation target onto the fundus oculi Ef, the reference light amount control information regarding the reduction of the amount of the reference light LR by the density filter 173, the dispersion correction parameter in the dispersion correction process of the tomographic image Ga, and so forth.

According to the fundus observation device 1, in the case of examination at and after the second time in the course observation or the like, the content of control of each part of the device applied in the past examination is automatically reproduced, so that the user is not required to perform a manual operation again such as an input operation for performing that control. Therefore, it becomes possible to easily perform the course observation or the like of the fundus oculi. Also, there is a merit that it is possible to prevent the occurrence of inadvertent mistakes due to performing a manual operation.

In addition, the examination can be performed in the same control pattern as in the past examination, so that it is possible to compare among the captured images under (almost) the same conditions when comparing the image obtained in the past examination and the image obtained in the examination this time. Consequently, such an effect that the accuracy of the course observation or the like improves can also be expected.

In addition, according to the fundus observation device 1 of the present embodiment, it is possible to reproduce the state of the device in the past examination by storing control information 213*a* for each patient and by selectively reading the control information 213*a* of the patient corresponding to the input patient identification information, which is operationally convenient.

In addition, according to the fundus observation device 1 of the present embodiment, when a plurality of sets of control information 213*a* regarding a certain patient are stored, the state of the device is reproduced by selectively employing the latest (last examination) control information 213*a*. In an actual course observation or the like, generally, a comparison between the results of the last examination and the results of the examination this time is most common. Therefore, the present embodiment is operationally convenient.

Modification

The configuration described above is merely one example to preferably implement the fundus observation device according to the present invention. Therefore, any modification may be implemented appropriately within the scope of the present invention.

For example, a fundus oculi image and a tomographic image are captured in a serial flow in the above embodiment (cf. steps S9 through S11 in FIG. 10), but there is a case of capturing a fundus image and a tomographic image separately. In this case, the content of control of each part of the device at the time of capture of a fundus image and the content of control of each part of the device at the time of capture of a tomographic image may differ from each other.

In such a case, it is configured to generate and store control information including both information representing the content of control of each part of the device at the time of capture of a fundus image (control information for fundus images) and information representing the content of control of each part of the device at the time of capture of a tomographic image (control information for tomographic images).

Then, at the time of capture of a new fundus oculi image, each part of the device is controlled based on the control information for fundus images of this control information, whereby the new fundus image is captured. On the other hand, at the time of capture of a new tomographic image, each part of the device is controlled based on the control information for tomographic images of the control information, whereby the new tomographic image is captured.

With this configuration, the content of control of each part of the device at the time of capture of a fundus image in the past is reproduced, so that it is possible, when capturing a new fundus image, to easily capture the fundus image in the course observation or the like, and to prevent the occurrence of inadvertent mistakes when capturing the fundus image. In addition, it is possible to capture the fundus image in the same control pattern as in the past examination, thereby making it possible to preferably compare fundus images.

Similarly, the content of control of each part of the device at the time of capture of a tomographic image in the past is reproduced, so that it is possible, when capturing a new tomographic image, to easily capture the tomographic image in the course observation or the like, and to prevent the occurrence of inadvertent mistakes when capturing the tomographic image. In addition, it is possible to capture the tomographic image in the same control pattern as in the past examination, thereby making it possible to compare tomographic images as desired.

In the above embodiment, the scan control information, the projection position control information, the reference light amount control information, and the dispersion correction parameter are included in the control information 213a. In the present invention, however, only at least one of these sets of information need to be included.

In addition, it is also possible to use control information 213a including content of control other than these sets of information.

For example, the polarization (polarization angle) of the signal light LS may be displaced due to the effect of the eye E, resulting in a mismatch with the polarization of the reference light LR. Then, a problem occurs in that the intensity of the interference light LC generated from these signal light LS and the reference light LR decreases, and a well-defined fundus image cannot be obtained.

In order to solve this problem, the fundus observation device may be provided with an optical member (polarization correction part) acting so as to match the polarization of the signal light LS with the polarization of the reference light LR. As examples of this polarization correction part, a Faraday rotator or the like can be employed.

For the fundus observation device having such a polarization correction part, information representing the correction state by the polarization correction part (e.g., in the Faraday rotator, the intensity of the magnetic field to be applied) in the case of having matched the polarization of the signal light LS with the polarization of the reference light LR by employing the polarization correction part when capturing a tomographic image is included in the control information 213a, which is stored on the information storage 213.

When a new tomographic image is captured for the same eye, the polarization correction part is controlled based on the information representing the correction state included in the stored control information 213a, whereby the correction state in the past is reproduced (in the Faraday rotator, the intensity of the magnetic field in the past examination is reproduced to correct the polarization).

With such a configuration, the correction state of the polarization of the signal light LS and the reference light LR at the time of capture of a tomographic image in the past are reproduced, so that it is possible, when capturing a new tomographic image, to easily capture a well-defined tomographic image in the course observation or the like, and prevent the occurrence of inadvertent mistakes when capturing the tomographic image. In addition, it is possible to capture the tomographic image in the same control pattern as in the past, thereby making it possible to preferably compare tomographic images.

In addition, it is possible to configure so as to, when performing the course observation or the like for two or more different sites of the fundus oculi for a patient, store control information such as the scan control information for each site. In this case, it is configured to store site identification information representing each site by associating with the control information, and to control each part of the device based on the control information associated with the site identification information input when performing a new examination. That makes it possible to reproduce the content of control of each part of the device for each site subject to examination.

In addition, it is possible to configure so as to, when performing the course observation or the like for two or more diseases and/or injuries of one patient, store control information for each disease and/or injury by associating with the disease and/or injury identification information, and to reproduce the content of control by controlling each part of the device based on the control information associated with the disease and/or injury identification information input when performing a new examination.

In addition, although each part of the device is controlled by selectively using the latest (last examination) control information 213a in the above embodiment, it is possible to configure so as to use the control information 213a in any examination in the past. Moreover, it is possible to configure so that the user can select and designate the control information 213a of past examinations (e.g., displaying the date and time of past examinations in a list or the like) and the content of control is reproduced by control of each part of the device based on the selected and designated control information 213a.

The fundus observation device according to the present invention has a fundus camera (unit) as a device forming a 2-dimensional image of the surface of the fundus oculi, but it may have a configuration in which a 2-dimensional image of the surface of the fundus oculi is formed by using any opthalmological equipment such as a slit lamp biomicroscope, for example.

Further, in the aforementioned embodiment, the image forming part 220 (image forming bard 208) performs the process of forming a 2-dimensional image of the surface of the fundus oculi Ef and a tomographic image, and the controller 210 (microprocessor 201, etc.) performs the controlling process, but it is possible to configure so that one or plural computers perform both the processes.

Furthermore, the program according to the present invention (control program 204a) can be stored on any computer-readable storage medium. Such a storage medium is, for example, an optical disk, a magneto optical disk (i.e., a CD-ROM, DVD-RAM, DVD-ROM, MO, etc.), a magnetic storage medium (i.e., a hard disk, Floppy® disk, ZIP, etc.), and a semiconductor memory.

As described above, it is configured to store control information representing content of control of the image-forming part when either a 2-dimensional image or tomographic image of the fundus oculi is formed, and to control the image-forming part based on the stored control information when the new one image described above is formed by the image-forming part, so that it is not necessary to again perform a manual operation such as an input operation for controlling the image-forming part when performing the second and subsequent examinations in a course observation or the like, whereby it becomes possible to facilitate the course observation or the like of the fundus oculi.

In addition, when performing an examination of the second time or more in a course observation or the like, the content of control of the image-forming part in the past is automatically reproduced, whereby it becomes possible to prevent possible inadvertent mistakes when inputting or the like via manual operation.

Furthermore, imaging at each time in a course observation or the like can be performed with the same content of control, whereby it becomes possible to preferably compare images in the course observation or the like.

What is claimed is:

1. A fundus observation device comprising:
an image forming part comprising a first image forming part and a second image forming part, the first image forming part forming a 2-dimensional surface image of fundus oculi of an eye through optical processing, the second image forming part comprising one or more galvanometer-mirrors to guide light to the fundus oculi by reflection so that the second image forming part optically scans a surface region of the fundus oculi corresponding to at least a part of the 2-dimensional surface image to form a tomographic image of the fundus oculi to form a 3-dimensional image;
a controller configured to change an arrangement of the galvanometer-mirror to control scanning of the surface region of the fundus; and
a storage configured to store the arrangement of the galvanometer-mirror as control information, when forming one of the 2-dimensional surface image and the 3-dimensional image is previously completed; and
an instruction part to instruct forming the image of the eye to be examined, wherein
the controller, at the time of instruction from the instruction part, is adapted to set the arrangement of the galvanometer-mirror to form a new one of the 2-dimensional surface image and the 3-dimensional image as indicated by the control information stored in the memory from the previously-completed image formation such that the control information is maintained over time from one image formation to the next image formation.

2. A fundus observation device according to claim 1, wherein the second image forming part comprises:
a light source;
an interference optical generator configured to split light emitted from the light source into signal light directed towards the fundus oculi and reference light directed towards a reference object and to generate interference light by overlapping the signal light passed through the fundus oculi and the reference light passed through the reference object;
a scanner comprising said one or more galvanometer-mirrors configured to scan a target position of the signal light to the fundus oculi in response to the instruction from the controller; and
a detector configured to receive the generated interference light to output a detection signal;
wherein the second image forming part forms the tomographic image of the fundus oculi, based on the detection signal, according to the scanning of the target position of the signal light,
wherein the control information includes scanning control information indicative of a scanning feature in which the scanner scans the target position of the signal light when the tomographic image is formed; and
wherein the controller, at the time of formation of a new tomographic image of the fundus oculi, controls the scanner to scan the target position of the signal light according to the scanning feature represented by the scanning control information.

3. A fundus observation device according to claim 2, wherein the scanner scans a target position of the signal light in a predetermined main scanning direction and a predetermined sub scanning direction perpendicular to the main scanning direction; and
wherein the second image forming part forms an image in the depth direction of the fundus oculi at each of the plurality of target positions along the main scanning direction, and forms the tomographic image along the main scanning direction based on the formed image in the depth direction, thereby forming the tomographic image at each of the two or more positions along the sub scanning direction.

4. A fundus observation device according to claim 2, wherein the scanning control information includes scanning position information indicative of a position for the target position of the signal light scanned by the scanner; and
wherein the controller, at the time of formation of the new tomographic image, controls the scanner to scan the target position of the signal light at the position represented by the scanning position information.

5. A fundus observation device according to claim 3, wherein the scanning control information includes scanning position information indicative of a position for the target position of the signal light scanned by the scanner; and
wherein the controller, at the time of formation of the new tomographic image, controls the scanner to scan the target position of the signal light at the position represented by the scanning position information.

6. A fundus observation device according to claim 3, wherein the scanning control information includes scanning track information indicative of a track in which the scanner scans the target position of the signal light; and
wherein the controller, at the time of formation of new tomographic image, instructs the scanner to scan the target position of the signal light in the track represented by the scanning track information.

7. A fundus observation device according to claim 2, wherein the scanner comprising said one or more galvanometer-mirrors includes one or more reflection mirrors that reflect the signal light and a mirror drive mechanism, the mirror drive mechanism changing the position of the one or more reflection mirrors in response to the instruction from the controller;
wherein the scanning control information includes information indicative of a position of the one or more reflection mirrors when the tomographic image is formed; and
wherein the controller, at the time of formation of the new tomographic image, instructs the mirror drive mechanism to change the position of the one or more reflection mirrors based on the scanning control information.

8. A fundus observation device according to claim 3, wherein the scanner comprising said one or more glavanometer-mirrors includes one or more reflection mirrors that reflect the signal light and a mirror drive mechanism, the mirror drive mechanism changing the position of the one or more reflection mirrors in response to the instruction from the controller;
wherein the scanning control information includes information indicative of a position of the one or more reflection mirrors when the tomographic image is formed; and
wherein the controller, at the time of formation of the new tomographic image, instructs the mirror drive mechanism to change the position of the one or more reflection mirrors based on the scanning control information.

9. A fundus observation device according to claim 4, wherein the scanner comprising said one or more glavanometer-mirrors includes one or more reflection mirrors that reflect the signal light and a mirror drive mechanism, the mirror drive mechanism changing the position of the one or more reflection mirrors in response to the instruction from the controller;

wherein the scanning control information includes information indicative of a position of the one or more reflection mirrors when the tomographic image is formed; and wherein the controller, at the time of formation of the new tomographic image, instructs the mirror drive mechanism to change the position of the one or more reflection mirrors based on the scanning control information.

10. A fundus observation device according to claim 5, wherein the scanner comprising said one or more glavanometer-mirrors includes one or more reflection mirrors that reflect the signal light and a mirror drive mechanism, the mirror drive mechanism changing the position of the one or more reflection mirrors in response to the instruction from the controller;

wherein the scanning control information includes information indicative of a position of the one or more reflection mirrors when the tomographic image is formed; and wherein the controller, at the time of formation of the new tomographic image, instructs the mirror drive mechanism to change the position of the one or more reflection mirrors based on the scanning control information.

11. A fundus observation device according to claim 6, wherein the scanner comprising said one or more glavanometer-mirrors includes one or more reflection mirrors that reflects the signal light and a mirror drive mechanism, the mirror drive mechanism changing the position of the one or more reflection mirrors in response to the instruction from the controller;

wherein the scanning control information includes information indicative of a position of the one or more reflection mirrors when the tomographic image is formed; and wherein the controller, at the time of formation of the new tomographic image, instructs the mirror drive mechanism to change the position of the one or more reflection mirrors based on the scanning control information.

12. A fundus observation device according to claim 1, wherein the image forming part comprises a fixation target projector configured to project to the fundus oculi a fixation target used for fixating the eye in response to the instruction from the controller;

wherein the control information includes projection information indicative of a projection position of the fixation target to the fundus oculi when the one of the images is formed; and wherein the controller, at the time of formation of the new one of the images of the fundus oculi, instructs the fixation target projector to project the fixation target to the fundus oculi based on the projection position represented by the projection information.

13. A fundus observation device according to claim 12, wherein the fixation target projector comprises:

a fixation target display configured to display the fixation target in response to the instruction from the controller; and projection optical system configured to project the displayed fixation target to the eye;

wherein the projection information includes information indicative of a display position at which the fixation target display displays the fixation target when the new one of the images is formed; and wherein the controller, at the time of formation of the new one of the images, controls the fixation target display to project the fixation target at the display position represented by the projection information.

14. A fundus observation device according to claim 1, wherein the second image forming part comprises:

a light source;

an interference optical generator configured to split light emitted from the light source into signal light directed towards the fundus oculi and reference light directed towards a reference object and to generate interference light by overlapping the signal light passed through the fundus oculi and the reference light passed through the reference object;

a filter provided on the optical path of the reference light to decrease an amount of the reference light;

a filter drive mechanism configured to rotate the filter in response to the instruction from the controller to change the decreasing amount of the reference light;

a detector configured to receive the generated interference signal to output a detection signal;

wherein the second image forming part forms the tomographic image of the fundus oculi based on the detection signal, wherein the control information includes reference light amount control information indicative of decreasing amount of the reference light when the tomographic image is formed; and wherein the controller, at the time of formation of new tomographic image of the fundus oculi, controls the filter drive mechanism to rotate the filter so that the amount of the reference light decreases by the amount represented by the reference light amount control information.

15. A fundus observation device according to claim 1, wherein the second image forming part comprises a dispersion corrector configured to correct an influence by dispersion of the eye at the formed tomographic image of the fundus oculi;

wherein the control information includes a correction parameter used for the correction of the influence by the dispersion at the tomographic image; and wherein the controller, at the time of formation of new tomographic image of the fundus oculi, instructs the dispersion corrector to correct the influence by the dispersion at the new tomographic image using the correction parameter.

16. A fundus observation device according to claim 1, wherein the second image forming part comprises:

a light source;

an interference optical generator configured to split light emitted from the light source into signal light directed towards the fundus oculi and reference light directed towards a reference object and to generate interference light by overlapping the signal light passed through the fundus oculi and the reference light passed through the reference object;

a polarization corrector configured to correspond a polarization direction of the signal light with a polarization direction of the reference light in response to the instruction from the controller; and a detector configured to receive the generated interference signal to output a detection signal, the generated interference signal being based on the signal light and the reference light after the polarization correspondence;

wherein the second image forming part forms the tomographic image of the fundus oculi based on the detection signal;

wherein the control information includes control instructions from the controller to the polarization corrector when the polarization directions correspond; and wherein the controller, at the time of formation of new tomographic image of the fundus oculi, controls the polarization corrector based on the control information stored in the storage.

17. A fundus observation device according to claim 1, further comprising an input part configured to input patient identification information,
wherein the storage stores the control information associated with the patient identification information; and
wherein the controller, at the time of formation of new tomographic image of the fundus oculi, controls the image forming part based on the control information associated with the patient identification information.

18. A fundus observation device according to claim 1,
wherein the storage stores the control information associated with the date information indicative of date and time of formation of one of the images by the image fixating part; and
wherein the controller, at the time of formation of new one of images of the fundus oculi, selects the latest control information among the control information based on the date information and controls the image forming part based on the selected latest control information.

19. A fundus observation device according to claim 1, wherein
the arrangement of the galvanometer-mirror set by the controller is an orientation of a reflection surface of the galvanometer-mirror.

20. A computer readable medium having computer readable code embodied therein for causing a computer system to perform a predetermined process, the computer having: a controller configured to change an arrangement of the galvanometer-mirrors to control scanning of the surface region of the fundus oculi; and a storage, the image forming part comprising a first image forming part and a second image forming part, the first image forming part forming a 2-dimensional surface image of fundus oculi of an eye through optical processing, the second image forming part comprising one or more galvanometer-mirrors to guide light to the fundus oculi by reflection so that the second image forming part optically scans a surface region of the fundus oculi corresponding to at least a part of the 2-dimensional surface image to form a tomographic image of the fundus oculi to form a 3-dimensional image,
wherein the predetermined process comprises:
storing the arrangement of the galvanometer-mirror as control information in a storage when forming one of the 2-dimensional surface image and the 3-dimensional image is previously completed;
instructing forming the image of the eye to be examined:
setting the image forming part to form a new one of the 2-dimensional surface image and the 3-dimensional image, in response to the instruction from the instruction part, as indicated by the control information from the previously completed image formation, such that the control information is maintained over time from one image formation to the next image formation.

* * * * *